United States Patent
Burdea et al.

(10) Patent No.: US 10,722,784 B2
(45) Date of Patent: Jul. 28, 2020

(54) BIMANUAL INTEGRATIVE VIRTUAL REHABILITATION SYSTEM AND METHODS

(71) Applicant: BRIGHT CLOUD INTERNATIONAL CORP., Highland Park, NJ (US)

(72) Inventors: Grigore Cristian Burdea, Highland Park, NJ (US); Doru Tadeusz Roll, Long Beach, NY (US); Nam-Hun Kim, Paramus, NJ (US); Kevin Abraham Polistico, Princeton, NJ (US); Ashwin Kadaru, Old Bridge, NJ (US)

(73) Assignee: Bright Cloud International Corporation, Highland Park, NJ (US)

( * ) Notice: Subject to any disclaimer, the term of this patent is extended or adjusted under 35 U.S.C. 154(b) by 0 days.

(21) Appl. No.: 15/669,952

(22) Filed: Aug. 6, 2017

(65) Prior Publication Data

US 2017/0361217 A1 Dec. 21, 2017

Related U.S. Application Data

(63) Continuation-in-part of application No. 14/032,360, filed on Sep. 20, 2013, now Pat. No. 9,724,598.
(Continued)

(51) Int. Cl.
*A63F 13/218* (2014.01)
*A63F 13/211* (2014.01)
(Continued)

(52) U.S. Cl.
CPC ........ *A63F 13/211* (2014.09); *A61B 5/02055* (2013.01); *A61H 1/00* (2013.01);
(Continued)

(58) Field of Classification Search
CPC . G06F 19/3481; A61B 5/1124; A61B 5/1125; A61B 5/02444; A63F 13/218
(Continued)

(56) References Cited

U.S. PATENT DOCUMENTS 6,334,778 B1    1/2002  Brown
6,454,681 B1 *  9/2002  Brassil .................. A63B 23/16
                                                    482/47
(Continued)

OTHER PUBLICATIONS

Wu, Cy, et al., "Randomized Trial of Distributed Constraint-Induced Therapy Versus Bilateral Arm Training for the Rehabilitation of Upper-Limb Motor Control and Function After Stroke," Neurorehabil Neural Repair, 2011, vol. 25(2), pp. 130-139 (10 pages).
(Continued)

*Primary Examiner* — Omkar A Deodhar
*Assistant Examiner* — Ross A Williams
(74) *Attorney, Agent, or Firm* — McCarter & English, LLP

(57) ABSTRACT

A system provides bi-manual game-based integrative therapy combining cognitive training with mild upper body physical exercising during game play. The system includes a pair of interfaces tracking a user's arms in 3D and detect trigger pressing. Custom therapeutic game controllers that detect grasping force, finger extension, 3D hand position, skin temperature and pulse may be used. Using one of these interfaces the patient plays a series of custom games displayed on a laptop, medical grade workstation, or other computer platform. The whole therapeutic system may be integrated on a medical cart, so to make the system mobile and easier to place in a clinical setting. Games were designed to improve motor control, shoulder strength, finger and arm range of motion, task sequencing, focusing, decision making (executive function), short term and long term visual/auditory memory, and were progressed in difficulty over 6 to 8 weeks of therapy. This therapy reduces depression.

23 Claims, 33 Drawing Sheets

Related U.S. Application Data

(60) Provisional application No. 61/869,857, filed on Aug. 26, 2013, provisional application No. 61/704,165, filed on Sep. 21, 2012.

(51) Int. Cl.
|  |  |
|---|---|
| *A61B 5/0205* | (2006.01) |
| *A63F 13/85* | (2014.01) |
| *A63F 13/20* | (2014.01) |
| *G16H 50/30* | (2018.01) |
| *G16H 40/63* | (2018.01) |
| *A61H 1/00* | (2006.01) |
| *G16H 20/30* | (2018.01) |
| *A61B 5/024* | (2006.01) |
| *A63F 13/42* | (2014.01) |

(52) U.S. Cl.
CPC ............ *A63F 13/06* (2013.01); *A63F 13/218* (2014.09); *A63F 13/85* (2014.09); *G16H 20/30* (2018.01); *G16H 40/63* (2018.01); *G16H 50/30* (2018.01); *A61B 5/02438* (2013.01); *A63F 13/42* (2014.09)

(58) Field of Classification Search
USPC ...................... 463/1–6, 35, 37, 40–42; 482/4
See application file for complete search history.

(56) References Cited

U.S. PATENT DOCUMENTS

| 9,724,598 | B2 | 8/2017 | Burdea |  |
|---|---|---|---|---|
| 2005/0113652 | A1* | 5/2005 | Stark | A61F 5/0125 600/300 |
| 2007/0087901 | A1* | 4/2007 | Brassil | A63B 23/16 482/44 |
| 2007/0136093 | A1 | 6/2007 | Rankin et al. |  |
| 2008/0281633 | A1 | 11/2008 | Burdea |  |
| 2012/0108909 | A1 | 5/2012 | Slobounov et al. |  |
| 2012/0157263 | A1* | 6/2012 | Sivak | G06F 3/014 482/4 |
| 2016/0038075 | A1 | 2/2016 | Burdea et al. |  |

OTHER PUBLICATIONS

Burdea, GC., "Virtual Rehabilitation-Benefits and Challenges," Methods Inf Med. 2003; vol. 42(5), pp. 519-523 (11 pages).
Brooks, CA., et al., "Traumatic Brain Injury: Designing and Implementing a Population-Based Follow-Up System," Arch Phys Med. Rehabil. 1997; vol. 78(8), pp. 26-30 (5 page).
Lin, KC., et al., "The Effects of Bilateral Arm Training on Motor Control and Functional Performance in Chronic Stroke: A Randomized Controlled Study," Neurorehabil Neural Repair, 2010; vol. 24(1), pp. 42-51 (11 pages).
Optale, G., et al., "Controlling Memory Impairment in Elderly Adults Using Virtual Reality Memory Training: A Randomized Controlled Pilot Study," Neurorehabil Neural Repair, 2010; vol. 24(4), pp. 348-357 (11 pages).
Burdea, GC., et al., "The Rutgers Arm II Rehabilitation System—A Feasibility Study," IEEE Trans Neural Sys Rehab Eng., vol. 18(5), pp. 505-514 (10 pages).
Burke, J.W., et al., "Optimising Engagement for Stroke Rehabilitation Using Serious Games," Vis. Comput, 2009, pp. 1085-1099, Springer Publishing (15 pages).
Rabadi, MH, et al., "Intensive Nutritional Supplements Can Improve Outcomes in Stroke Rehabilitation," Neurology, 2008, pp. 1856-1861. AAN Enterprises (7 pages).
Roger, VL., et al., "Executive Summary: Heart Disease and Stroke Statistics—2012 Update: A Report from the American Heart Association," Circulation, 2012; vol. 125(1), pp. 188-197 (12 pages).
Cauraugh, JH., et al., "Bilateral Movement Training and Stroke Motor Recovery Progress: A Structured Review and Meta-Analysis," Hum. Mov. Sci., 2010; vol. 29(5), pp. 853-870 (25 pages).
Ausenda, CD., et al., "Transfer of Motor Skill Learning from the Healthy Hand to the Paretic Hand in Stroke Patients: A Randomized Controlled Trial," Eur. J. Rehabil Med., 2011; vol. 47(3), pp. 417-425 (9 pages).
Wang, M., et al., "Neuronal Basis of Age-Related Working Memory Decline," Nature, 2011; vol. 476(7359), pp. 210-213 (13 pages).
Duncan, PW., et al., "Reliability of the Fugl-Meyer Assessment of Sensorimotor Recovery Following Cerebrovascular Accident," Phys Ther., 1983; vol. 63(10), pp. 1606-1610 (16 pages).
Sixense Entertainment, Razer Hydra Master Guide, pp. 1-11, 2011 (11 pages).
CNet Leap Motion Controller Review: Virtual Reality for Your Hands, Jul. 22, 2013 http://www.cnet.com/products/leap-motion-controller/ (9 pages).
Cameirao MS, et al., "The Rehabilitation Gaming System: A Review,". Stud Health Technol Inform. 2009;145:65-83. Review. PubMed PMID: 19592787 (19 pages).
Liu, Huajun, et al. "Realtime human motion control with a small number of inertial sensors." Symposium on Interactive 3D Graphics and Games. ACM, 2011 (8 pages).
Cameirao, et al., "Neurorehabilitation Using the Virtual Reality Based Rehabilitation Gaming System: Methodology, Design, Psychometrics, Usability and Validation" 2010 (14 pages).
Notice of Allowance dated Apr. 7, 2017, issued in connection with U.S. Appl. No. 14/032,360 (8 pages).
Office Action dated Sep. 9, 2016, issued in connection with U.S. Appl. No. 14/032,360 (17 pages).
Office Action dated Jan. 12, 2016, issued in connection with U.S. Appl. No. 14/032,360 (13 pages).
Office Action dated Aug. 24, 2018, issued in connection with U.S. Appl. No. 14/841,042 (11 pages).
Office Action dated Oct. 6, 2017, issued in connection with U.S. Appl. No. 14/841,042 (9 pages).

\* cited by examiner

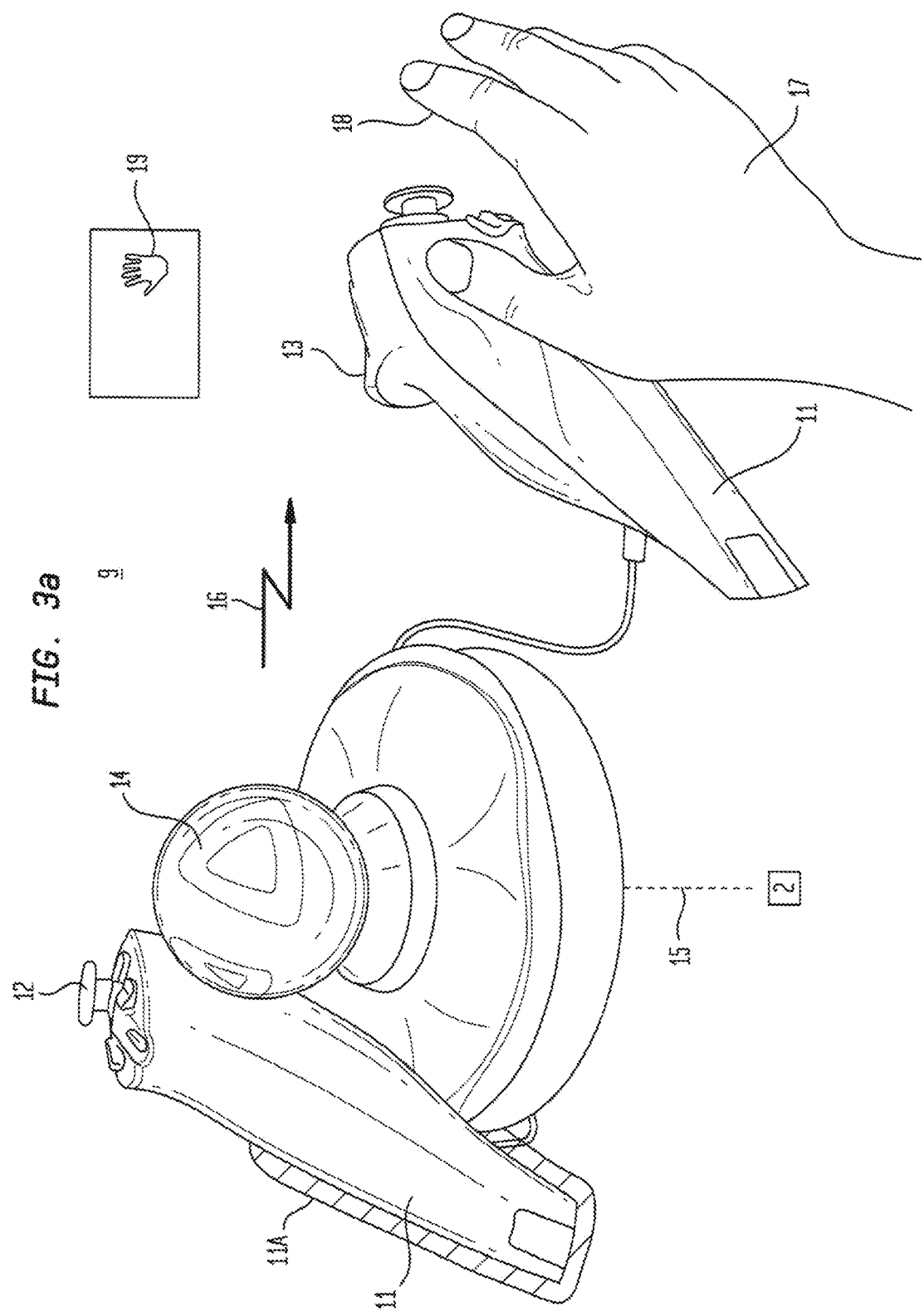

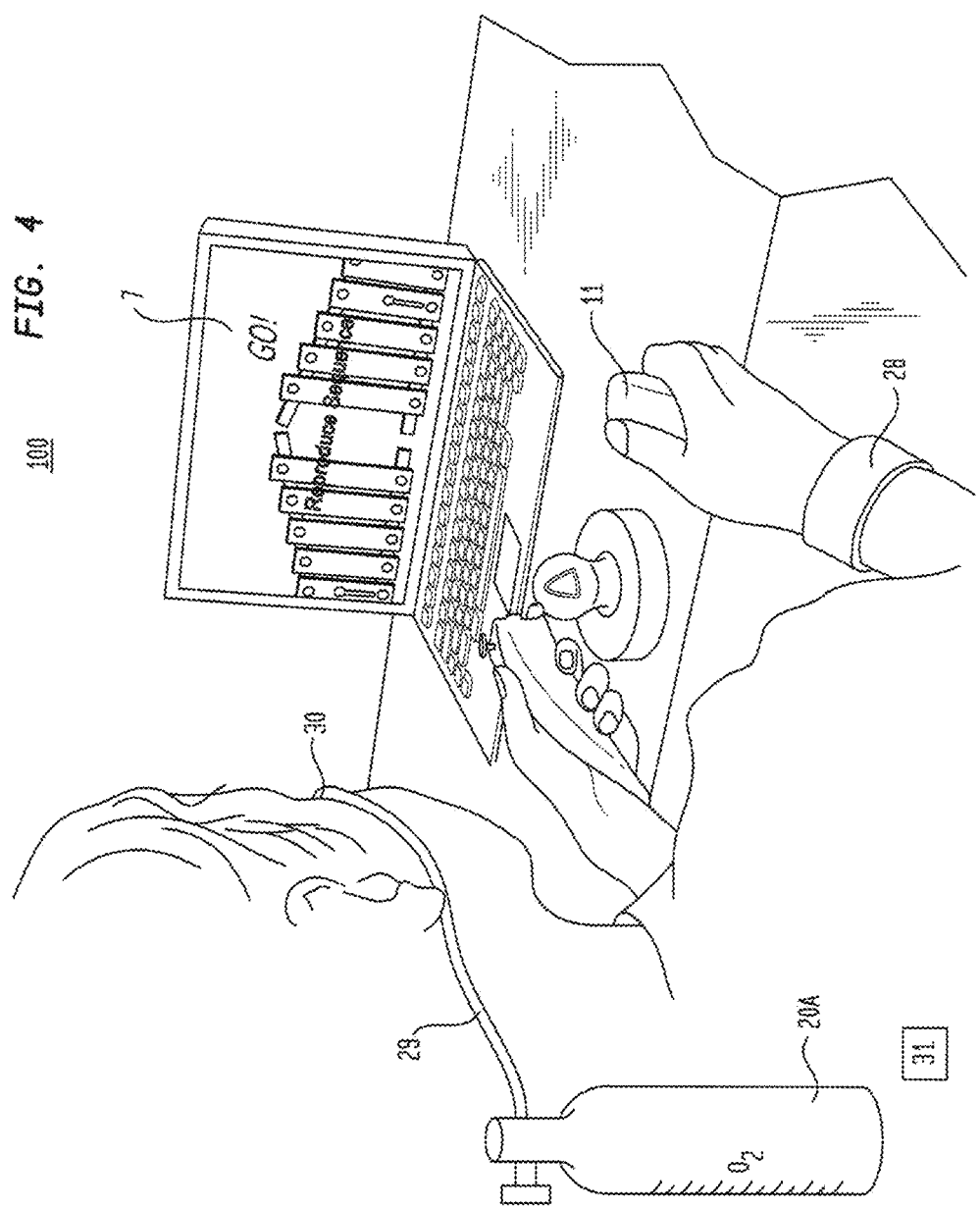

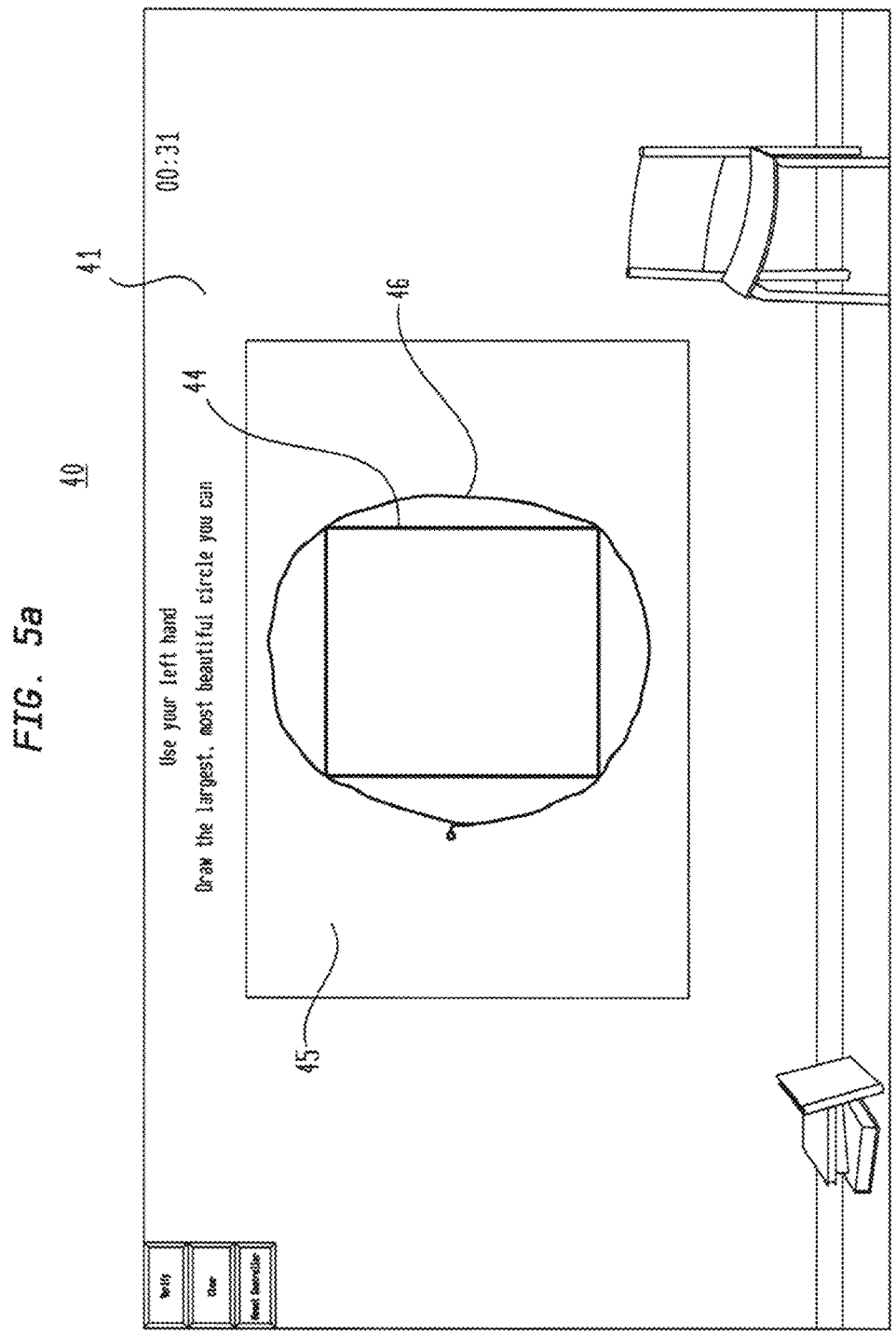

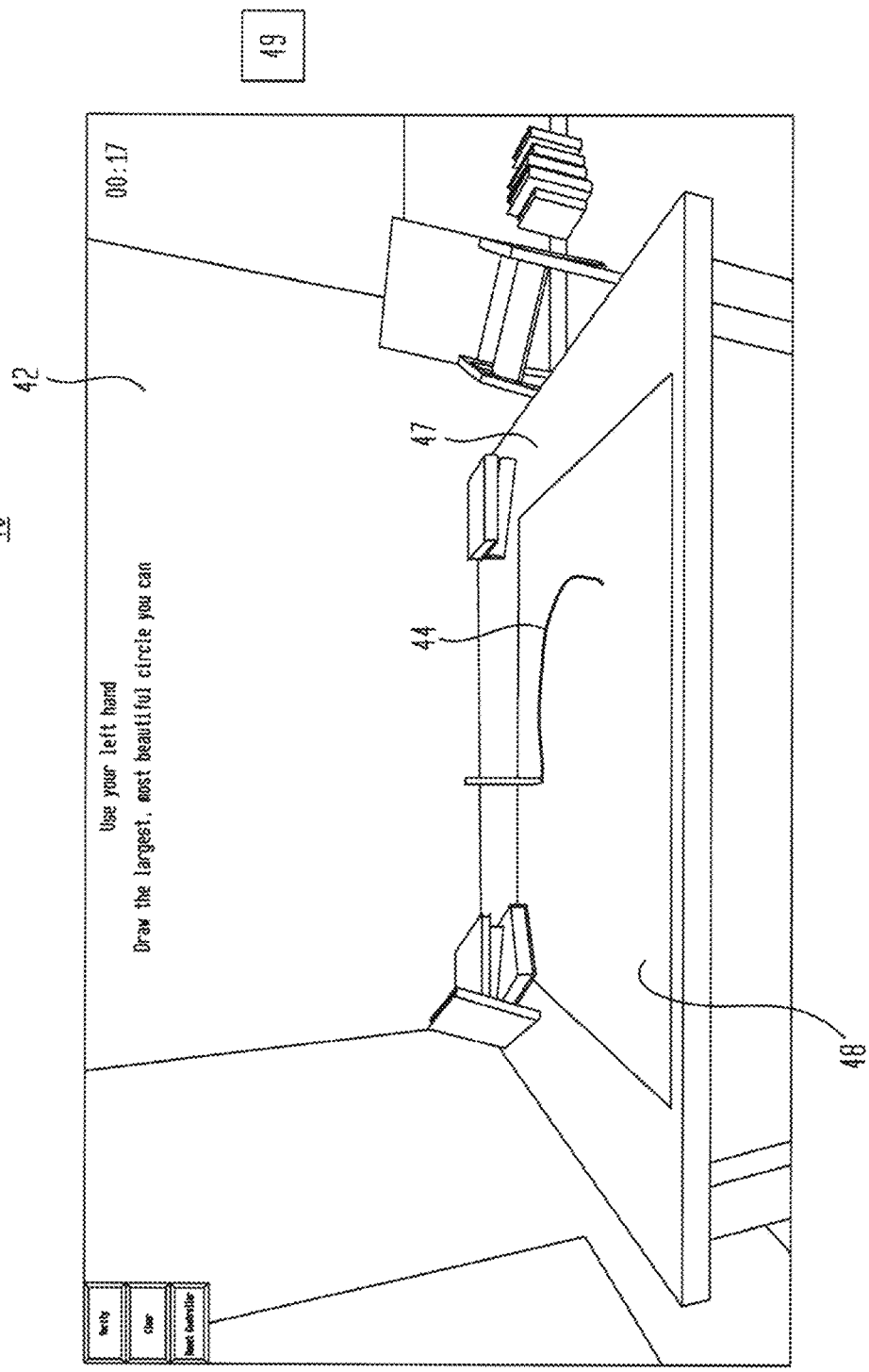

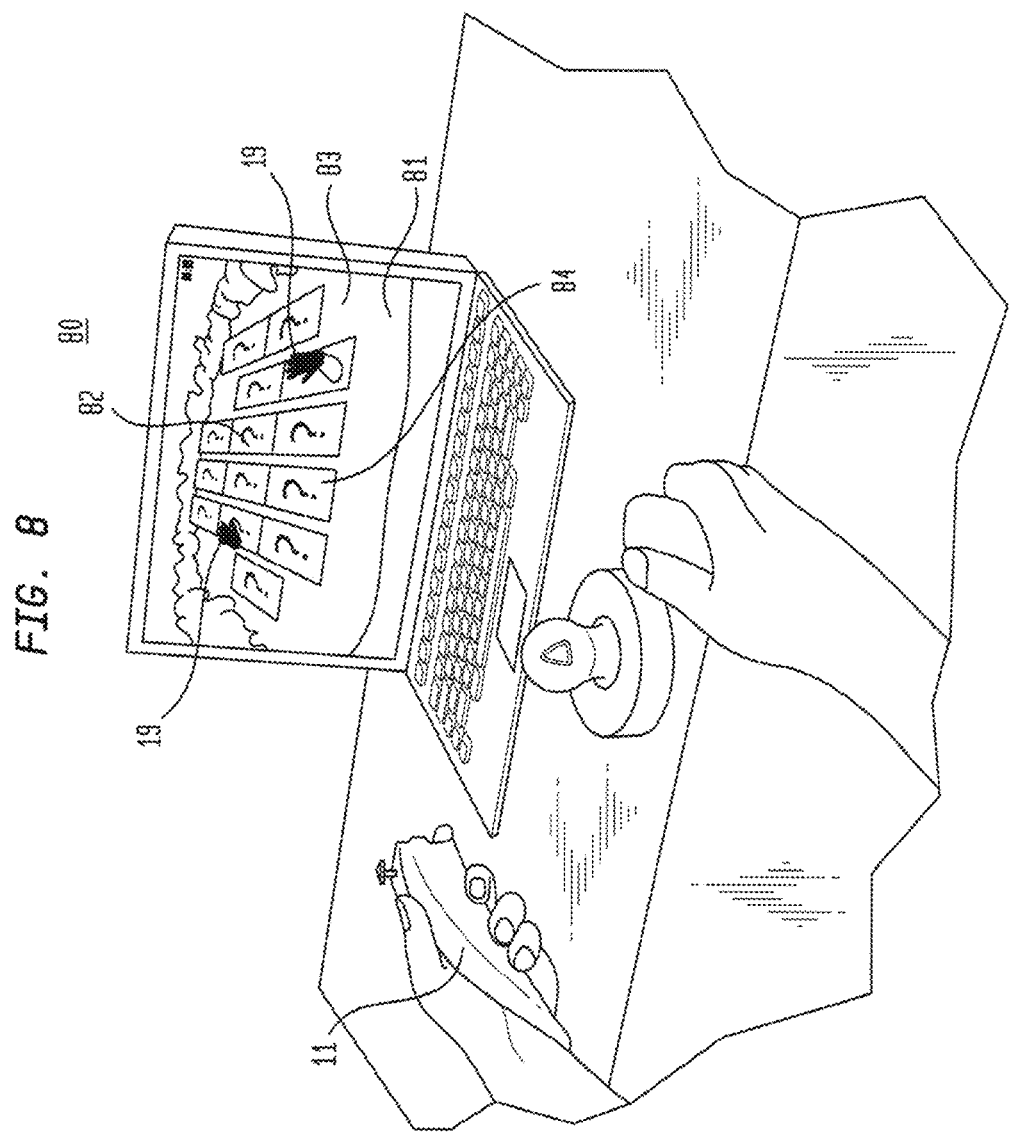

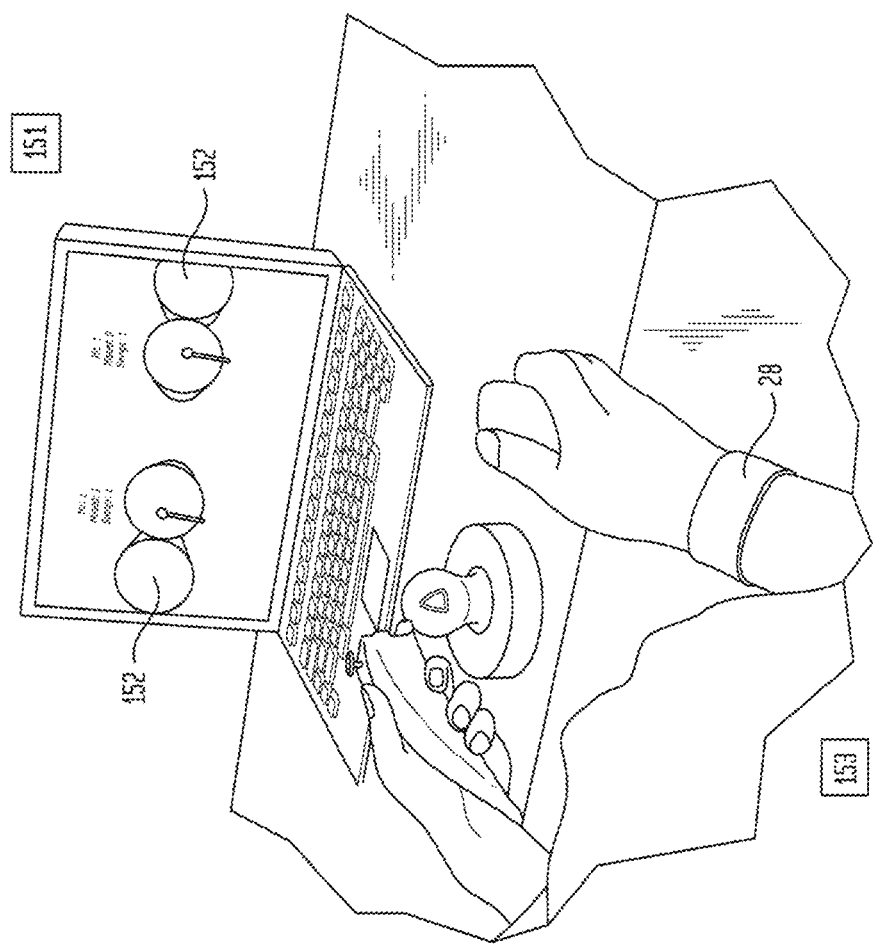

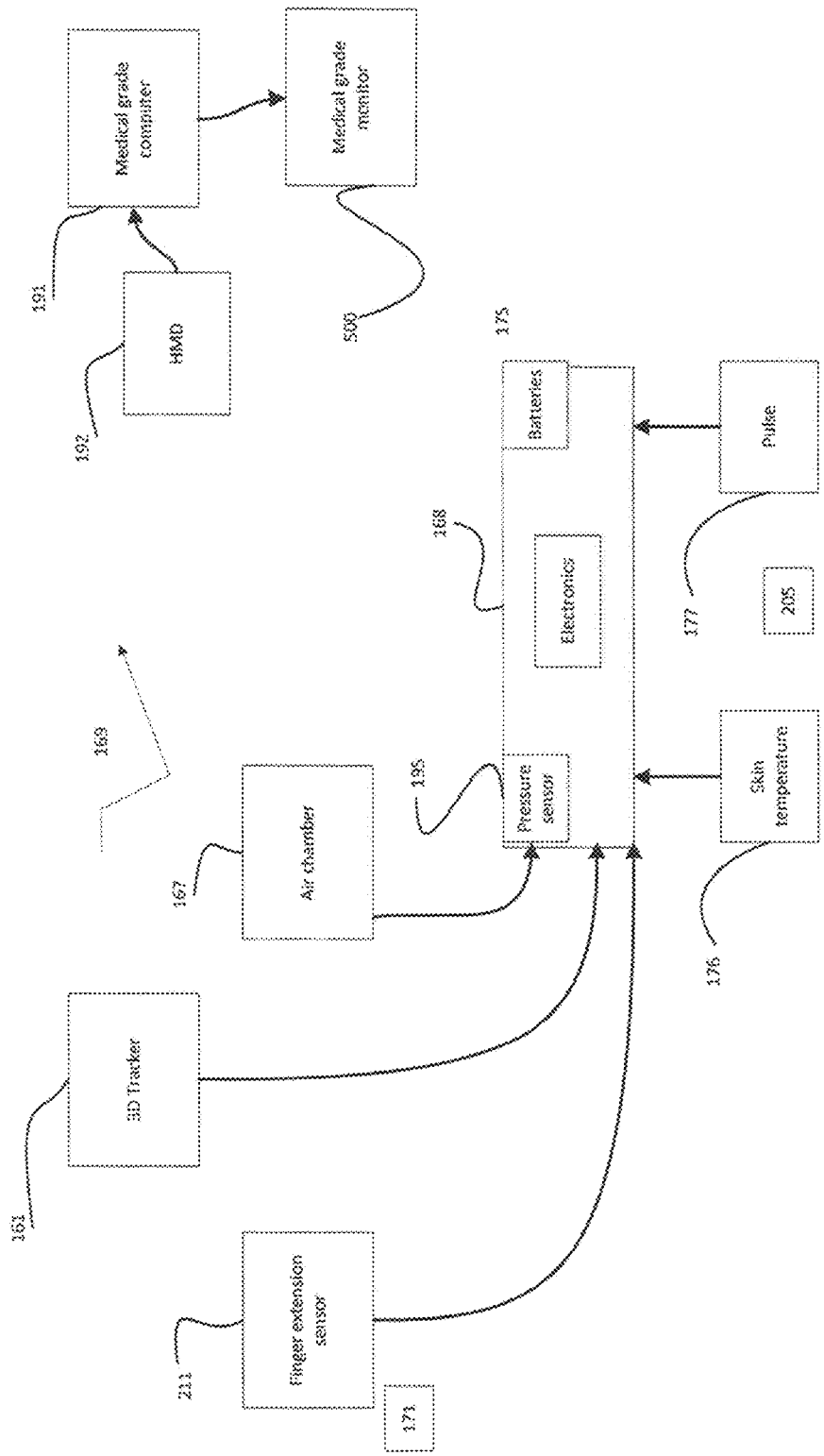

BIMANUAL INTEGRATIVE VIRTUAL REHABILITATION SYSTEM AND METHODS

CROSS REFERENCE TO RELATED APPLICATIONS

The present application is a Continuation In Part of U.S. Non-provisional patent application Ser. No. 14/032,360, filed Sep. 20, 2013, which claims the benefit of and priority to U.S. Provisional Patent Application No. 61/704,165, filed on Sep. 21, 2012, and also claims the benefit of and priority to U.S. Provisional Patent Application No. 61/869,857, filed on Aug. 26, 2013, all of which are hereby fully incorporated herein by reference in their entirety.

This invention of the present application was made with government support under Grant 1R43AG052290-01 awarded by the National Institutes of Health. The invention described in U.S. Non-provisional patent application Ser. No. 14/032,360 was made with government support under Grant 9R44AG044639-02A1 awarded by the National Institutes of Health. The government has certain rights in the inventions.

BACKGROUND

Stroke is the leading cause of disability in the US, with 795,000 Americans suffering one each year. See Reference No. 1. (all references are listed at the end of the specification). Traditional physical rehabilitation of the paretic arm involves passive movement, compensatory training on the less involved arm, electrical stimulation, to which more recently has been added constraint induced therapy to combat learned non-use of the hemiplegic hand. See Reference No. 2. These are uni-manual training approaches involving a single arm which do not take into account the prevalence of activities of daily living (ADLs) which involve both arms.

Another drawback of uni-manual training is diminished neural cross talk to mirror motor areas associated with bimanual activities. A meta analysis of 48 stroke studies to determine the cumulative effect of bilateral arm training on motor capabilities post-stroke (Reference No. 3) did however find a significant effect post training involving bimanual repeated reach movements timed to auditory cues. Another argument in favor of bilateral training is a randomized controlled study of stroke patients at the end of their outpatient therapy. See Reference No. 4. Researchers found, for the first time, that training the healthy arm (in a pegboard filling task) resulted in a 23% functional improvement in the non-trained paretic arm. Researchers also observed improvement in bilateral tasks performance in the experimental group. The control group, which did not train, had no significant difference from baseline. These studies point to the untapped advantages of bimanual training and motivate the present application.

It is known in the art that numerous task-related repetitions are needed to produce changes in the brain. Repetitions, while necessary to induce recovery through brain plasticity, can lead to lack of engagement (attendance to task) by the patient. Second only to the amount of practice, feedback on performance is a key element in motor training and a way to engage the patient. Knowledge of performance feedback can be provided by the therapist (present next to the patient), or through graphics in a virtual rehabilitation setting (Reference No. 5), where the therapist may be remote. Virtual rehabilitation benefits focus, motivation, and provides substantially more intensive training than customary care.

Stroke survivors, as well as other patient populations (such as those post severe traumatic brain injury) present with both motor and cognitive deficits. See Reference No. 6. Typically their short term and long term memory are affected, as are decision making (executive function), and the ability to focus. Most stroke patients also get depressed. Under the current fractionated care system, such patients are attended by therapists, as well as psychologists or psychiatrists, in separate sessions. This care delivery method is costly and does not exploit fully the body-mind continuum. As opposed to patients who are post-traumatic brain injury and predominantly young, the elderly form the majority of stroke survivors. For them, the situation worsens due to age related cognitive decline. See Reference No. 7. One age related cognitive deficit is associated with diminished ability for split attention (or dual-tasking). These patients need a system designed from the start for integrative cognitive and motor therapy, in order to minimize costs and maximize outcomes. Such system would use therapeutic games that pose both cognitive and whole arm motor demands, and train grasping in dual tasks. The system should automatically adapt to the patient's functioning level, thus making games winnable, so to improve morale (reduce depression). Games, such as cognitive games, mediate many repetitions, so to facilitate improvement or at least maintenance of motor and cognitive function over time. Users that benefit most are the elderly with mild cognitive impairment (MCI) developing into dementia (Reference No. 8).

There are indications that bimanual training induces higher functional improvements compared to uni-manual training. A randomized controlled study (Reference No. 9) was performed on patients who were chronic post-stroke, half doing bimanual training and the controls doing training of the affected arm, with some coping mechanism (assistance) from the other arm. While both groups had the same training duration and intensity, those doing bimanual training had a 9 points larger improvement in motor function (as measured by their Fugl Meyer Assessment [Reference 10] scores) vs. controls. Another randomized study of 36 nursing home residents was performed to try to lessen cognitive decline and improve memory function. See Reference 11. The experimental group showed significant improvements in long-term recall and in several other aspects of cognition, while controls showed progressive decline. The above findings motivate the system described here, a bimanual therapy system that simultaneously addresses motor and cognitive impairments of patients post-stroke, post TBI, or those with MCI developing into dementia. This novel integrative therapy uses custom, adaptable, bimanual virtual reality games, which combine into gradated therapy sessions.

SUMMARY

In accordance with one embodiment, systems and methods of providing therapy to a patient having a first arm, a first hand, a second arm and a second hand, are provided. In accordance with an aspect of the method, the following steps are performed: a video game is executed on a computer and action from the video game is portrayed on a display, and through sound, the action being viewed and heard by the patient. Then, the patient holds a first component of a game controller in the first hand and manipulates a button on the first component of the game controller with the first hand and moves the first component of the game controller with the first hand and the first arm to control the video game. Alternately, the patient can squeeze a deformable element on the first component of a game controller, or extend fingers against a movable lever of the same first component of the game controller. The patient may hold first arm in an arm support with a curved low-friction underside, said forearm support being connected to the first component of the game controller. This allows the arm holding the first component of the game controller to pronate or supinate while supported on a surface. In one embodiment, the first component of the game controller incorporates sensors to measure the skin temperature and pulse of the first arm of the patient. In one embodiment, the skin temperature sensor and pulse sensor are attached to the forearm support. In one embodiment, the patient also holds a second component of a game controller in the second hand and manipulates a button on the second component of the game controller with the second hand. The patient moves the second component of the game controller with the second hand and the second arm to control the video game. Alternately, patient can squeeze a deformable element on the second component of a game controller, or extend fingers against a movable lever of the same second component of the game controller. The patient may hold second arm in an arm support with low-friction, curved underside, said forearm support being connected to the second component of the game controller. It is appreciated that in one embodiment the curved forearm support may be a shell in the form of a half cylinder. This allows the arm holding the second component of the game controller to pronate or supinate while supported on a surface. In one embodiment, the second component of the game controller incorporates sensors to measure the skin temperature and pulse of the second arm of the patient. In one embodiment, the first component of the game controller is separate from the second component of the game controller and can be moved independently from the second component of the game controller. The game controller sends one or more signals to the computer. In one embodiment, the one or more signals are sent to the computer in real time. These signals are representative of a position of the button on the first component, of a position of the button on the second component, of a motion of the first component in 3D space and of a motion of the second component in 3D space, of the squeezing of a deformable element of the first component of the game controller, of the squeezing of a deformable element of the second component of the game controller, of the rotation of a lever of the first component of the game controller, of the rotation of a lever of the second component of the game controller, or of the pronation/supination of the arm holding the first component of the game controller and the pronation/supination of the second arm holding the second component of the game controller, or of the skin temperature and pulse of the arm holding the first component of the controller, or of the skin temperature and pulse of the arm holding the second component of the game controller. These signals are reported by the game controller to the computer in real time. The computer analyzes the one or more signals and controls one or more video games to control avatars and perform actions portrayed on the display and heard on computer speakers.

In accordance with another embodiment, the video game causes a displayed object to include one of two codes wherein a first code indicates that the displayed object can be moved with the first component of the controller and a second code indicates that the displayed object can be moved with the second component of the controller. The two codes can be, for example, different object or avatar colors.

In accordance with one embodiment, when the video game causes a displayed object to include one of two codes, the computer only allows the displayed object to be moved by either the first component or the second component of the controller in accordance with the two codes. In one embodiment, the object and the avatar controlled by a component of the controller have matching colors.

In one embodiment, objects depicted on the screen may have the same color/appearance, but have different "hardness." This perceived hardness is a sensorial illusion (also referred to as a induced haptic illusion), produced by mapping the amount of squeezing of the hand controller deformable element and the corresponding deformation of the object the hand avatar grasps on the screen. An object will appear "hard," when a strong squeezing is required to minimally deform the grasped virtual object. Conversely, an object will appear "soft" when a light squeezing of the deformable element of the game controller (such as just touching it with the fingertips) produces a substantial deformation of the virtual object shown on the screen. Thus, a haptic illusion of object hardness can be induced.

In accordance with one embodiment, the computer monitors and stores a set of information from the first component and the second component of the controller, the set of information including: (1) number of activations of the button on the first component of the controller; (2) number of movements of the first component of the controller, (3) number of squeezes of the deformable element for the first component of the first controller; (4) number of movements of the rotating lever of the first component of the controller, (5) number of pronations/supinations of the first component of the game controller; (6) number of activations of the button on the second component of the controller; and (7) number of movements of the second component of the controller (8) number of squeezes of the deformable element for the first component of the first controller; (9) number of movements of the rotating lever of the first component of the controller, (10) number of pronations/supinations of the first component of the game controller. It is envisioned that the activation, squeezes, and movement counts are totals for a therapy session. In one embodiment, the computer then controls the video game and resulting action is presented on the display in accordance with the set of information. The computer can also analyze the set of information to determine progress of the patient by assigning scores to each video game, by counting the number of repetitions performed by the first component and by the second component of the controller. Furthermore, patient progress may also be analyzed based on training intensity, namely the number of repetitions in a given duration of time (ex. repetitions/minute). It is further appreciated that the computer can use these data to automatically generate a therapy session report.

In one embodiment, while holding the first and second components of the controller the patient wears wrist weights on one or both forearms. The patient may also be provided with extra oxygen through a flexible tube to the nose, so to increase oxygenation to the brain. The patient may consume food supplements designed to increase cognitive activity immediately prior to using the first and second components of the controller during video game play.

In one embodiment, the computer controls the action displayed such that the action caused by the first component of the controller is the same as the action caused by the second component of the controller.

Systems that perform the methods described herein are also provided. For example, a system can also include a computer, a video game executing on the computer, a display portraying action from the video game, the action being viewable and heard by the patient, a game controller having a first hand-held component with a button, a deformable element, a rotating lever, a skin temperature sensor and a pulse sensor and a second hand-held component with a button, a deformable element, a rotating lever, a skin temperature sensor and a pulse sensor wherein the first component is separate from the second component and can be moved independently from the second component The game controller sends one or more signals representative of a position of the button on the first component, of a position of the button on the second component, of a motion of the first component and of a motion of the second component, or the amount of movement of the rotating lever of the first component of the controller, or the amount of movement of the rotating lever of the second component of the controller, or the amount of squeezing of the deformable element of the first component of the controller, or the amount of squeezing of the deformable element of the second component of the controller, the skin temperature and pulse of the arm holding the first component of the game controller, and the skin temperature and pulse of the arm holding the second component of the game controller, which are reported by the game controller in real time to the computer. In one embodiment, the computer analyzes the one or more signals and controls the video game to control action portrayed on the display such that the action caused by the first component of the controller is the same as the action caused by the second component of the controller.

In one embodiment the computer can use data on patient game performance to generate a report for the clinician. In a related embodiment the computer keeps track of exercise time and stops further game play when a set duration had been reached.

In one embodiment, the computer can also cause all other processes described herein.

In one embodiment, the controller may be a Leap Motion controller, in which case the patient interacts with the computer through hand gestures.

In one embodiment, the controller may be an off-the-shelf VIVE game controller.

In one embodiment the controller may be a custom design in which a VIVE tracker is integrated with a deformable element, a rotating lever, and a low-friction rounded forearm support.

In one embodiment, some or all of these therapeutic games may be played with wrist weights, so to increase the physical exercise component of the integrative therapy. For elderly users smaller weight values (such as 0.5 lb, 1 lb and 2 lb) are appropriate for use with the system described in this application.

In one embodiment, weights can be applied to a handheld controller that is manipulated by the patient.

DESCRIPTION OF THE DRAWINGS

FIG. 3a illustrates a Razer Hydra bimanual game interface.

FIG. 4 illustrates a patient playing a game while wearing wrist weights and having an oxygen tube to the nose.

FIG. 5a illustrates an arm vertical movement baseline.

FIG. 5b illustrates an arm horizontal movement baseline.

FIG. 8 illustrates a Card Island game to train short term visual memory and auditory memory.

FIG. 14a illustrates a Musical Drums bimanual game.

FIG. 18 depicts a block diagram of the electronic and sensing elements of the therapeutic game controller of FIGS. 15 and 16.

DESCRIPTION

Figure 1:
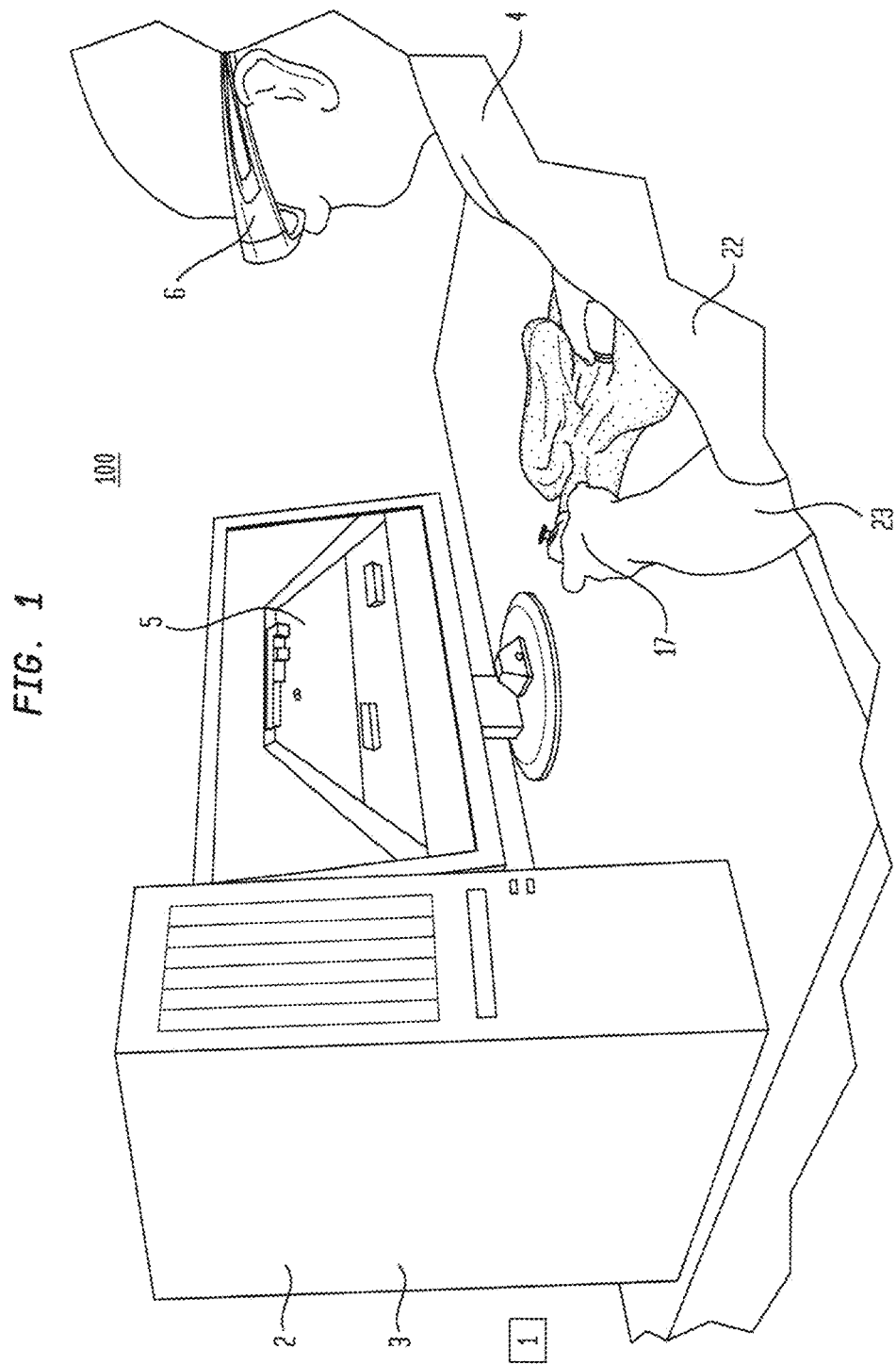
FIG. 1 illustrates a bimanual exercise system using a workstation, 3D (stereo) monitor, 3D glasses, and Hydra bimanual hand controller.

Referring to FIG. 1, the bimanual therapy system 100 consists of off-the shelf gaming hardware and a library of custom therapeutic games 1 written in Unity 3D Pro. See Reference 12. The games are rendered on a computer 2, such as those available in commerce. For example the games 1 can be rendered by an HP Z600 graphics workstation with an nVidia "Quadro 2000" graphics accelerator 3 (FIG. 1). It is appreciated that any consumer grade graphics card used in rendering games may be used instead of the Quadro 2000 one. In one embodiment the graphics are in 3D, so to facilitate immersion and help the patient 4 (also referred to as a user) in his manual tasks. Therefore the workstation 2 is connected to an Assus VG236H 3D monitor 5, and the patient 4 wears a pair of nVidia "3D Vision" active stereo glasses 6.

Figure 2:
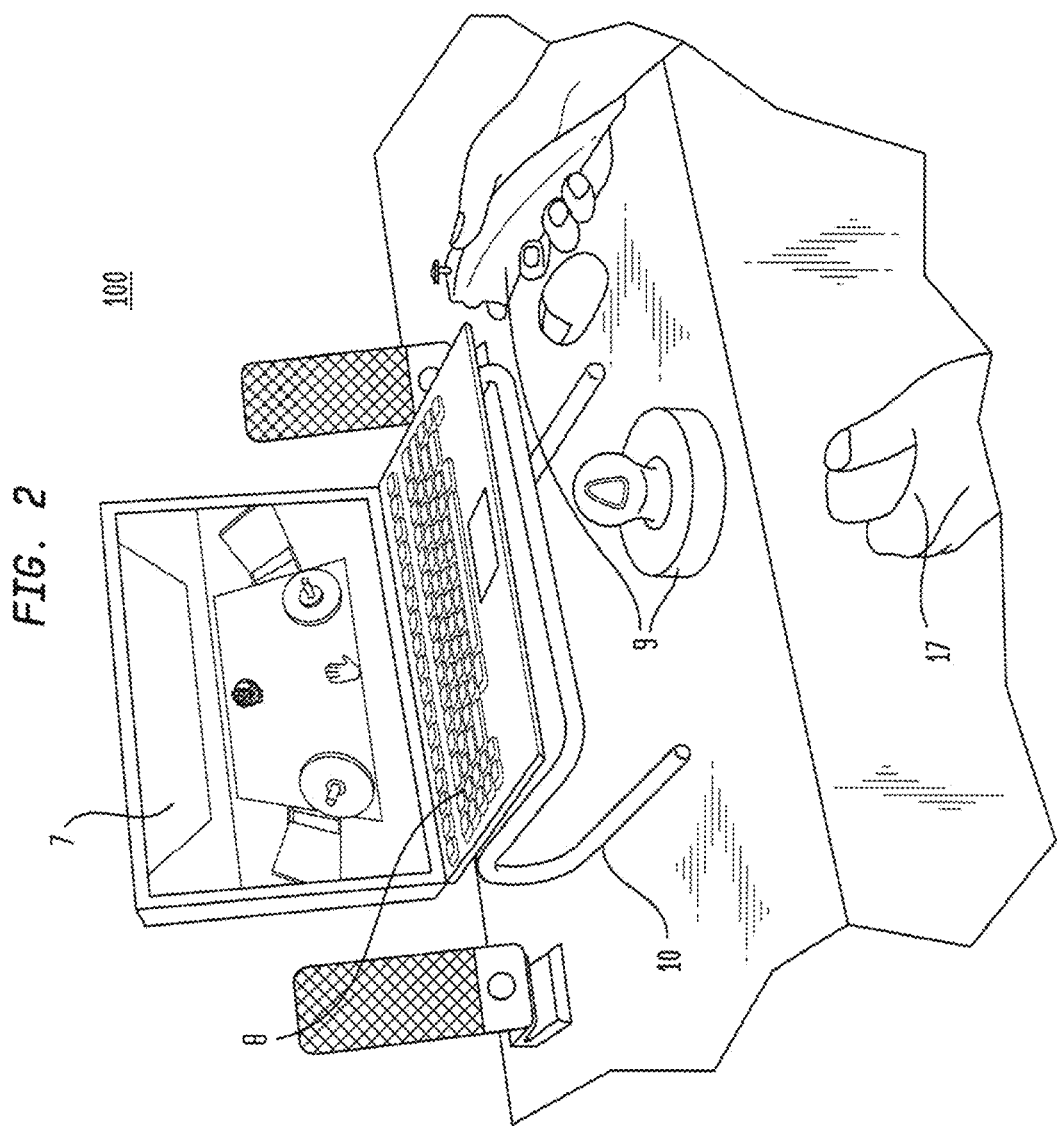
FIG. 2 illustrates a system using a gamer laptop placed on a cooling tray and the same Hydra bimanual hand controller.

Alternately the games 1 may be rendered on a 2D "gamer" laptop computer 7 such as the HP Envy with 17 in screen and nVidia GeForce GT 750M graphics accelerator 8. The same bimanual game controller 9 may be used (FIG. 2), and the laptop 7 may be placed on a cooling tray 10, such as those available commercially. It is envisioned that other computers may be used as part of the bimanual integrative therapeutic system 100.

In one embodiment, the interaction with the games is mediated by a Razer Hydra bimanual interface (Reference 13) shown in FIG. 3a. It consists of two hand-held pendants 11, each with a number of buttons 12 and a trigger 13, and a stationary source 14 connected to the workstation 2 over an USB port 15. The source 14 generates the magnetic field 16 which allows the workstation 2 to track the 3D position and orientation of each hand 17 in real time. Of the many buttons on the pendants 11, the system 100 uses an analog trigger 13 so to detect the degree of flexion/extension of the patient's index fingers 18. The pressing of these analog triggers 13 controls the closing/opening of hand avatars 19, while the position/orientation of the hand avatars 19 is determined by the position/orientation of the corresponding Hydra pendants 11. The Hydra is calibrated at the start of each session by placing the two pendants 11 next to the source 14. Its work envelope is sufficient to detect hand 17 position for a patient 4 exercising in sitting.

Weights 11A can be provided which can be slipped over the pendant 11 to increase the exercise difficulty for the patient. The weights can be provided in a variety of forms and they can be attached to the pendants 11 (both sides) by snaps, Velcro, and other mechanical attachments.

Figure 3B:
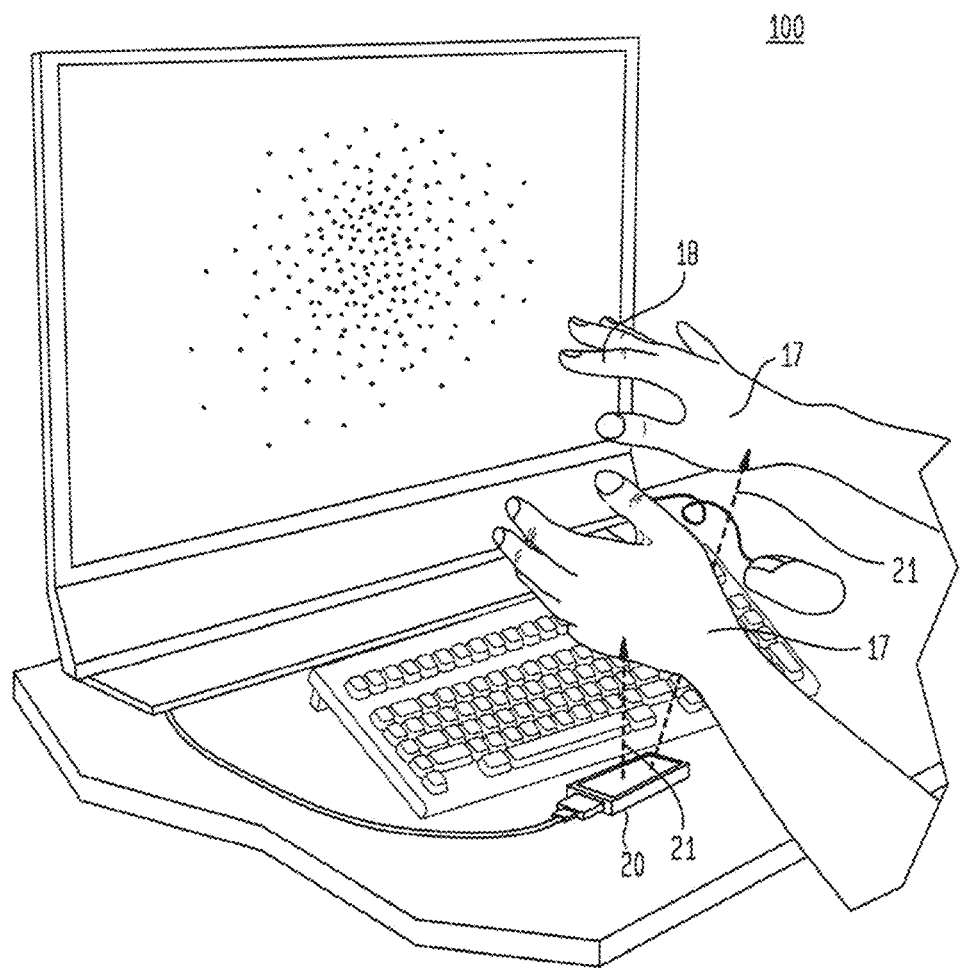
FIG. 3b illustrates a Leap Motion hand controller.

Alternately the system 100 can use a Leap Motion hand controller 20, as shown in FIG. 3b (see Reference 14). In this case the interaction is through hand 17 gestures, without the need for pendants 11. Detection of hand 17 and finger 18 movement is through infrared beams 21 emitted by the controller 20 and reflected off the hands 17 of the patient 4.

Figure 3C:
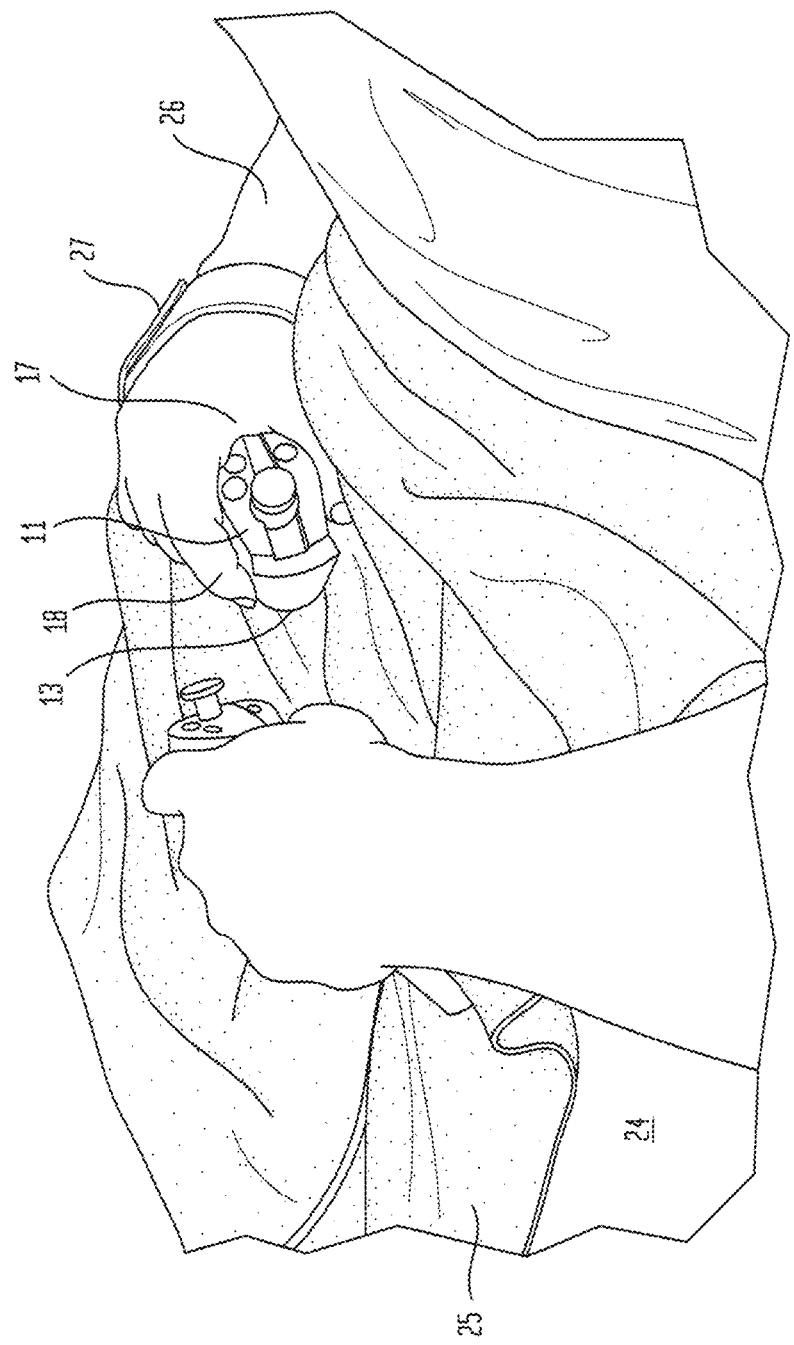
FIG. 3c illustrates a Velcro strip used to keep Hydra controller in the hand of a stroke patient with the forearm resting on a towel.

Stroke patients 4 in the acute stage (just after the neural infarct) have weak arms 22. Similarly, patients who are chronic post-stroke may have low gravity bearing capability. Some of them may also have spasticity (difficulty flexing/extending elbows 23, or fingers 18). Thus using the Hydra 9 with this population is different from use in normal play by healthy individuals. The adaptation in the present application is to place the weak arm 22 on a low-friction table 24, and use a small towel 25 under the forearm 26, so to minimize friction and facilitate forearm 26 movement. Furthermore, for spastic patients who may have difficulty holding the Hydra pendant 11 in their spastic hand 17, the solution is to use Velcro strips 27 to position the index finger 18 properly over the analog trigger 13 (see FIG. 3c).

Figure 3D:
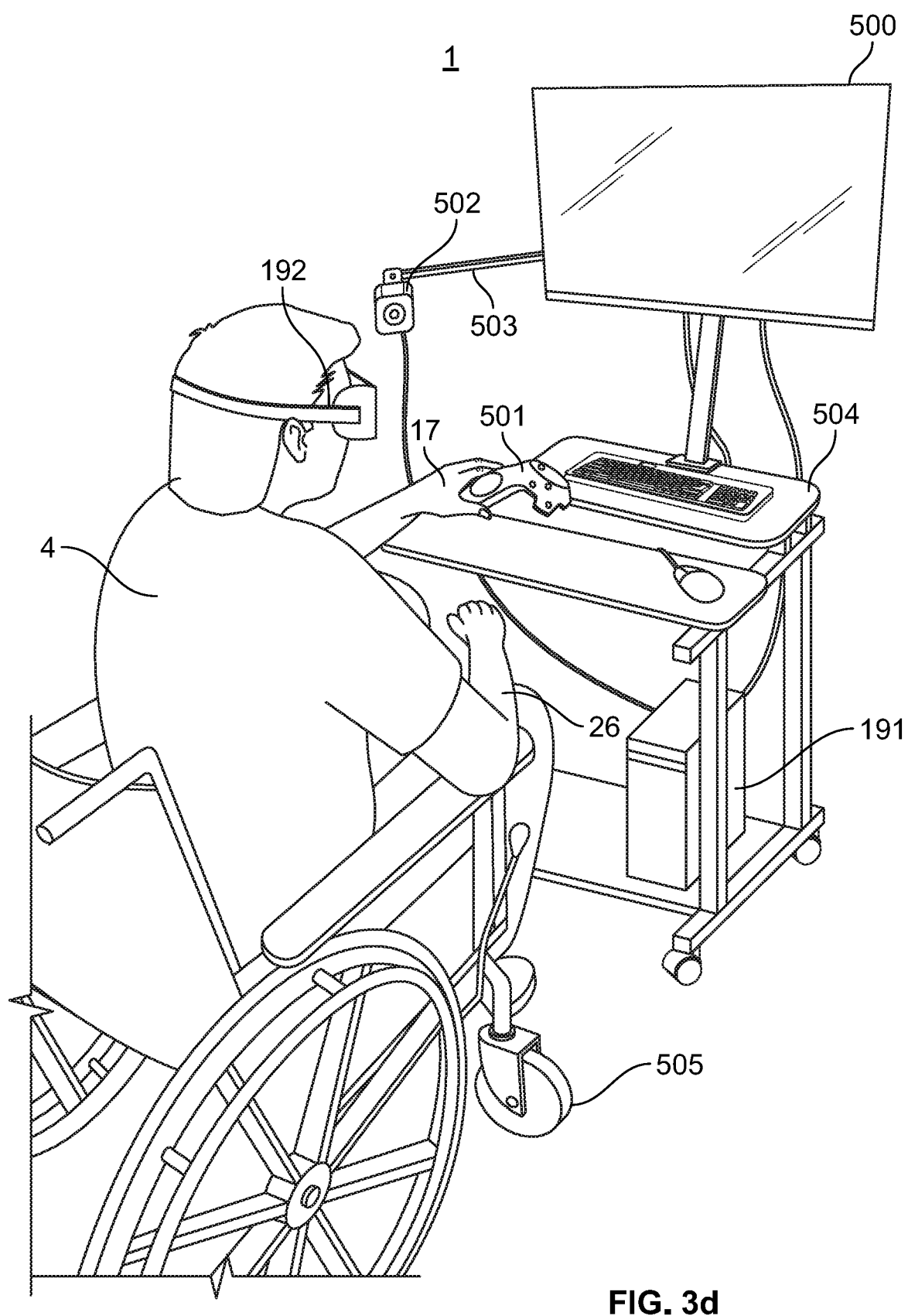
FIG. 3d illustrates the VIVE hand controllers incorporated with a computer cart, arms supporting two VIVE infrared illuminators, a computer, a computer display, a printer, and patient in wheelchair.

In one embodiment, the game controller may be one or a pair of wireless VIVE controllers 501 illuminated by a pair of infrared illuminators 502 (see FIG. 3d). The illuminators 502 are mounted on a supporting beam 503 and arranged left and right of a display 500 connected to a computer 191. The display 500 presents one or a multitude of games 1, meant to rehabilitate patient 4. In one embodiment, the display 500 and computer 191 are medical grade. The computer 191, infrared illuminators 502 and medical grade display 500 are placed on a computer cart 504, such that the whole rehabilitation system assembly is self-contained and mobile. It is envisioned that patient 4 may be sitting in a wheelchair 505, holding two game controllers such as the VIVE 501. The movement of the patient 4 arms 26 and hand 17 is tracked in real time and data transmitted wirelessly to a head mounted display (HMD) 192 connected to the computer 191.

Figure 3E:
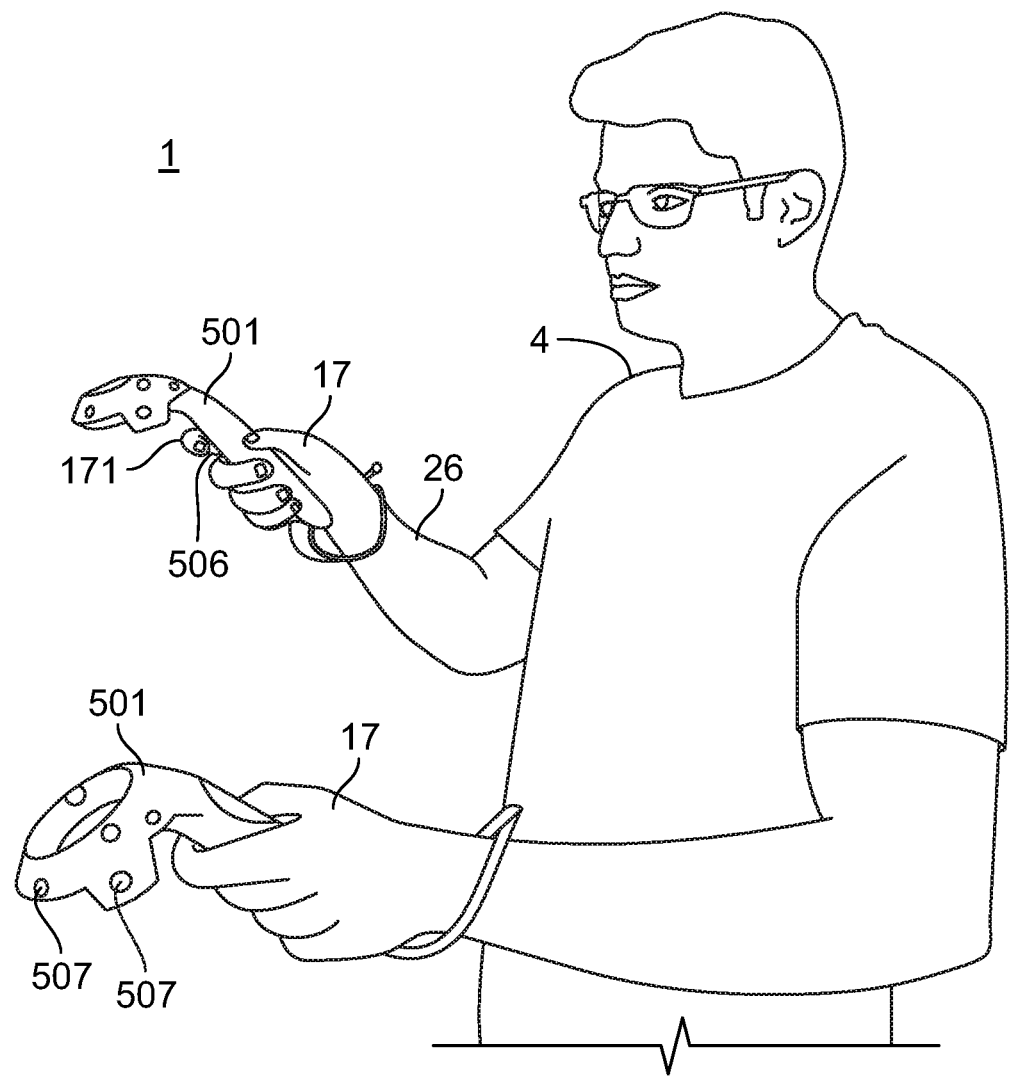
FIG. 3e is a detailed view of a patient holding two VIVE hand controllers and pressing their triggers with index fingers.

FIG. 3e shows patient 4 exercising while standing. Patient 4 holds one VIVE controller 501 in each hand 17, such that index finger 171 is resting on top of a trigger button 506. It is appreciated that flexing and extending finger 171 will cause the closing and opening of hand avatar 19 in games 1. The tracking of VIVE controllers 501 is based on data provided by infrared sensors 507 illuminated by infrared illuminators 502 (FIG. 3d). Patient 4 (FIG. 3d) should have gravity bearing capability in his arms 26 in order to hold and move controllers, such as VIVE 501 without requiring a low-friction supporting table 24.

For stronger patients 4, or those without motor impairment to their arms 22 or hands 17, it is possible to play the games 1 while wearing wrist weights 28. The amount of added physical exertion is proportional to the size of weights 28, as well as the duration of the session played while wearing the wrist weights 28. It is appreciated that elderly users 4 will feel more comfortable while wearing smaller weights 28 (0.5 lb, 1 lb, 2 lb). FIG. 4 shows a patient 4 playing a game 1 using the Hydra pendants 11, while wearing wrist weights 28. It is envisioned that the size of the wrist weights 28 may be increased over the weeks of training, with larger weights worn in later weeks.

It is further envisioned that while playing the cognitive games 1 on the system 100 which now has the commercial name of BrightBrainer™, the patient 4 can also have an Oxygen tube 29 to the nose 30. The Oxygen tube 29 is of the type known in the art (transparent plastic), being small and flexible, and unencumbering to the user 4. Provision of extra Oxygen to the blood, brings extra oxygenation to the brain. This boosts the brain activity, as it facilitates energy generation and in turn helps neuronal activity. The oxygen is provided via a tank 30A.

In addition to (or instead of) wearing an Oxygen tube 29, the patient 4 may choose to have food supplements 31 (such as dark chocolate, fatty fish, spinach, berries, walnuts, avocado, water intake increase, wheat germs, beats, garlic). Such food supplements 31 need to be taken some time before the play on the system 100, so to be metabolized, and facilitate increased cognitive activity.

Therapeutic Games

Several games 1 were developed to be played either uni-manually or bimanually. This gives flexibility when the therapy focus is motor re-training (using uni-manual mode), or integrative cognitive retraining (using bimanual mode).

The requirement for developing a multi-game 1 therapy system 100 stems from the need to address several cognitive areas (by targeted games 1), as well as to minimize boredom by alternating games 1 during a session.

In a sequence of sessions, the first sessions can be played uni-manually so patients 4 learn the games 1. In the second part they progress to using both arms 22, and finally to wearing weights 28 for increased exercising demands. It is also envisioned that in a sequence of sessions, the duration of play will be shorter in the first sessions, and progressively longer over the duration of therapy.

Baselines

Each patient 4 is different, each day. It is therefore necessary to use baselines 40 to determine the patient's 4 motor capabilities, and adapt the games 1 accordingly. In one embodiment, the system 100 uses at least five baselines, two for arm range 41, 42, one for the index finger flexion/extension 43 using the analog trigger 13 on the Hydra pendant 11, or VIVE game controller 501 and one for forearm 23 pronation and one for forearm 23 supination. More or less baselines may be used based on specific movements and/or abilities of a patient that are to be measured. As seen in FIG. 5a, the vertical baseline 41 asks the patient 4 to draw a circle 44 on a virtual blackboard 45. The software then fits a rectangle to the "circle" 44 and this range is used to map the arm 22 limited vertical range 46 to the full vertical space on the game 1 scene. The horizontal baseline 42 (FIG. 5b) is similar, except now the patient 4 is asked to draw a circle 44 on a virtual table 47 covered by a large sheet of paper 48.

During bimanual play sessions each arm 22 performs the baselines 42, and 42 in sequence, and each arm 22 has different gains 49 mapping real movement to avatar 19 movement in the virtual scene. Thus the movement of their respective hand avatars 19 appears equal (and normal) in the virtual world, something designed to motivate the patient 4. A further reason to present exaggerated movement of the paretic arm 22 when mapped to VR is the positive role image therapy has traditionally played. In other words, the patient 4 is looking at the display 5, not at the hand 17, and believes what he or she sees on the display. This technique is similar by that developed by Burdea et al. in U.S. application Ser. No. 12/422,254 "Method for treating and exercising patients having limited range of body motion," which is incorporated herein by reference. (See Reference 15).

Figure 5C:
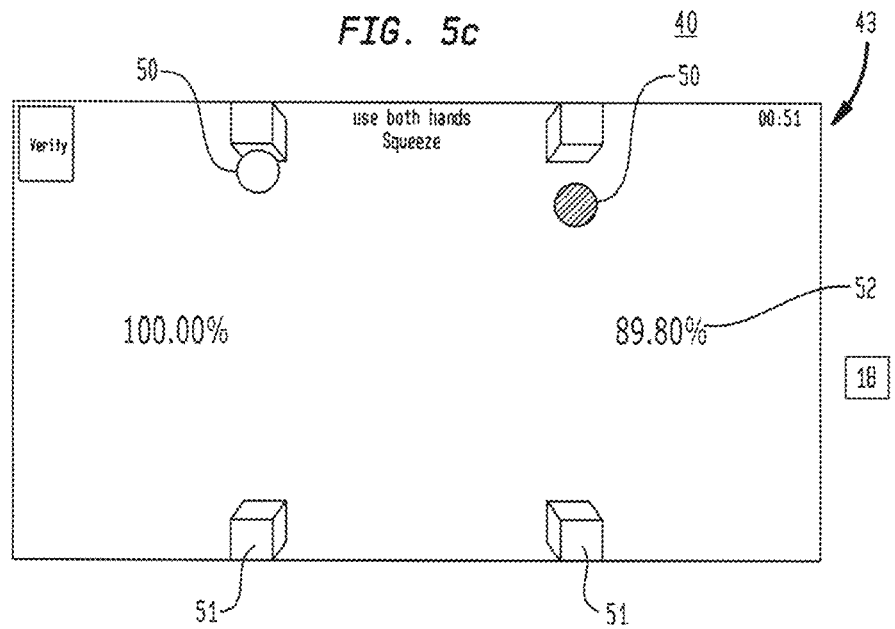
FIG. 5c illustrates a flexion baseline for left and right index fingers.
Figure 5D:
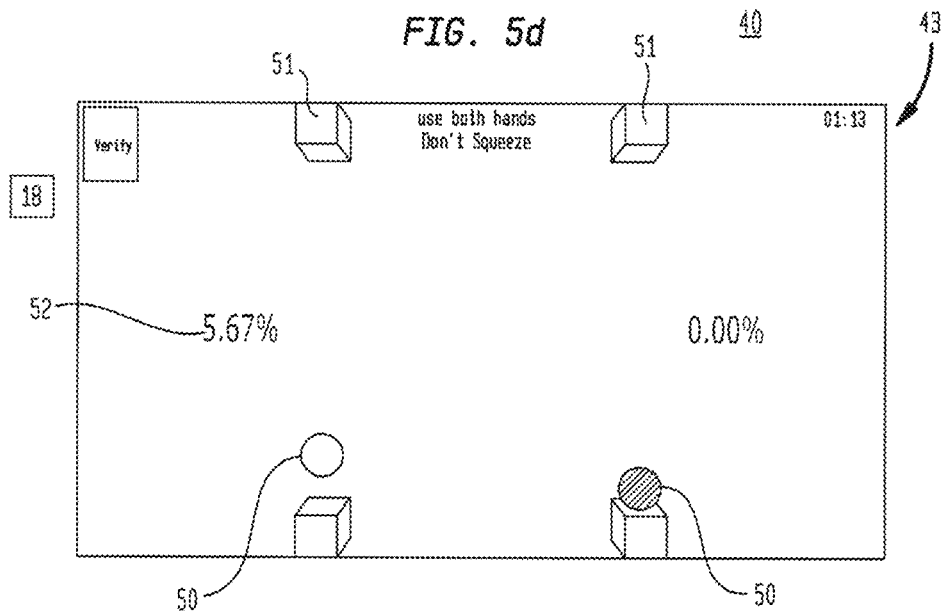
FIG. 5d illustrates an extension baseline for left and right index fingers.

The third baseline 43 measures the range of movement of the index 18 of each hand 17. Unlike the range baselines 41 and 42, done in sequence, the index baseline 43 is done simultaneously for both hands 17. As seen in FIG. 5c, the patient sees two spheres 50 that move vertically between target blocks 51, in proportion with the index 18 movement on each pendant trigger 13. First the patient 4 is instructed to flex, and the two balls 50 move up a certain percentage of full range. The baseline displays the finger-specific percentage 52 of full motion. Subsequently the patient 4 is asked to extend the index 18 of each hand 17 and the balls 50 move down, again a certain percentage of full range 52 (FIG. 5d). For spastic patients 4 the paretic index 18 will have little difficulty flexing, but substantial difficulty extending. The resulting limited range for the paretic index 18, and full range of the non-paretic one are then mapped to the hand avatars 19. The two hand avatars 19 will thus show full flexing and full extension during the games 1.

Figure 5E:
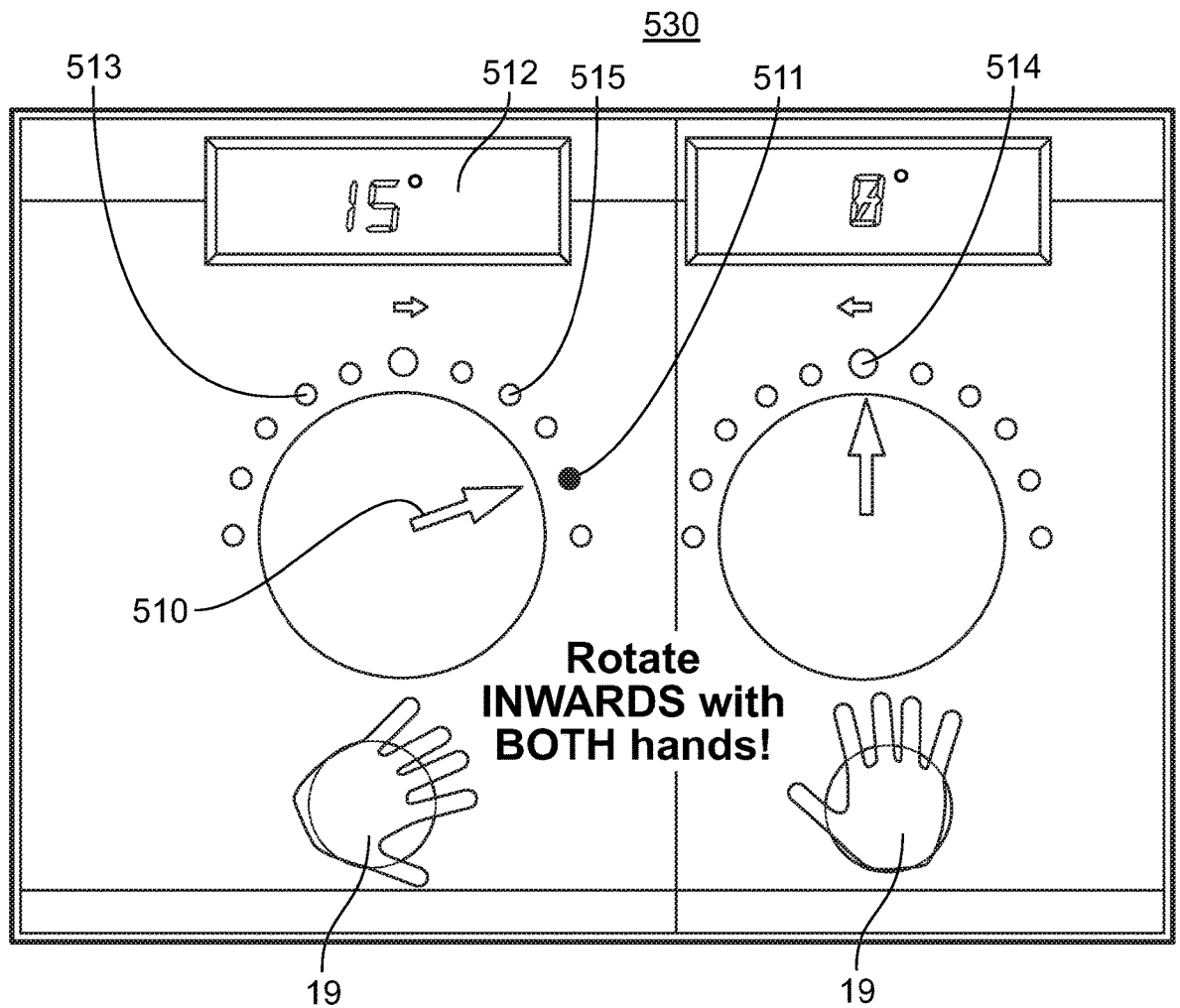
FIG. 5e illustrates the pronation baseline of the left or right forearm.
Figure 5F:
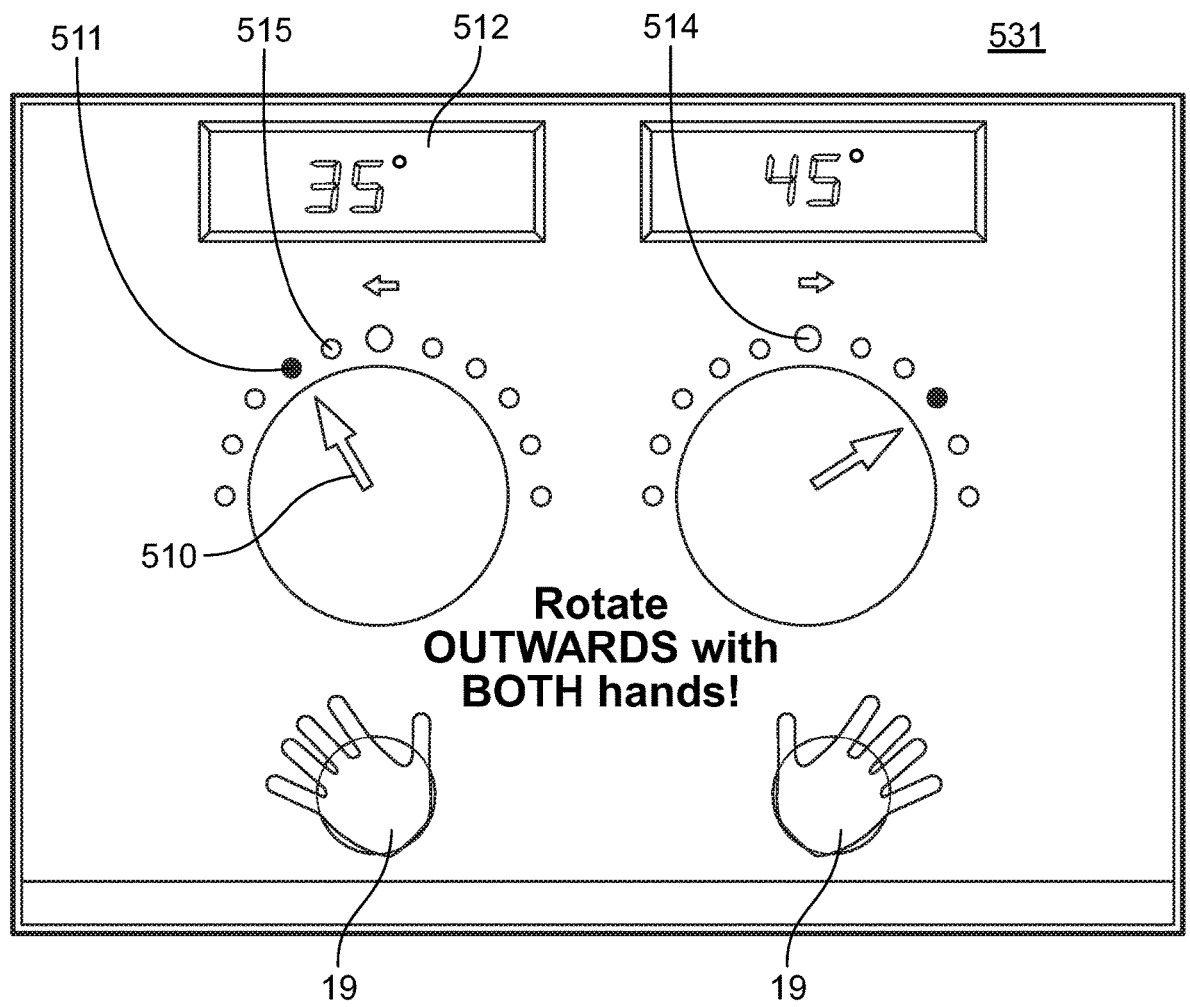
FIG. 5f is the supination baseline of the left or right forearm.

Certain patients 4 may need to exercise the movement of their forearms 26 in pronation (rotating the forearm 26 inwards), or supination (rotating the forearm 26 outwards). Pronation baseline 530 (FIG. 5e) and supination baseline 531 (FIG. 5f) are used to map limited range of pronation/supination movements of patient's forearms 26 to full rotation range of hand avatars 19 in games 1. In pronation baseline 530 and supination baseline 532, the degree of rotation is visualized graphically by clock-like dials 510 rotating in synchronicity with hand avatars 19. Numerically the same rotation angle is displayed digitally by digital display 512. The clock-like display 510 has a number of beads 513 that change color based on the achieved range of pronation/supination rotation of forearm 26. For example the bead 511 in FIG. 5e corresponds to a maximal pronation, and will have one color. Other beads 515 located on clock-like display 510 between neutral position 514 and maximal pronation rotation bead 511 will have a different color. Pronation baseline (FIG. 5e) will have two clock-like displays 510 and two digital displays 512, corresponding to the rotation of left and right forearms 26 of patient 4. Supination baseline 531 (FIG. 5f) will have a similar visualization arrangement, however the direction of forearm 26 rotation is opposite that done in pronation baseline 530. The color of beads 513 will also follow the same convention used in pronation baseline 530, with bead 511 corresponding to maximal supination angle having one color, and beads 515 located between neutral position bead 514 and maximal position bead 511 having a different color.

Figure 5G:
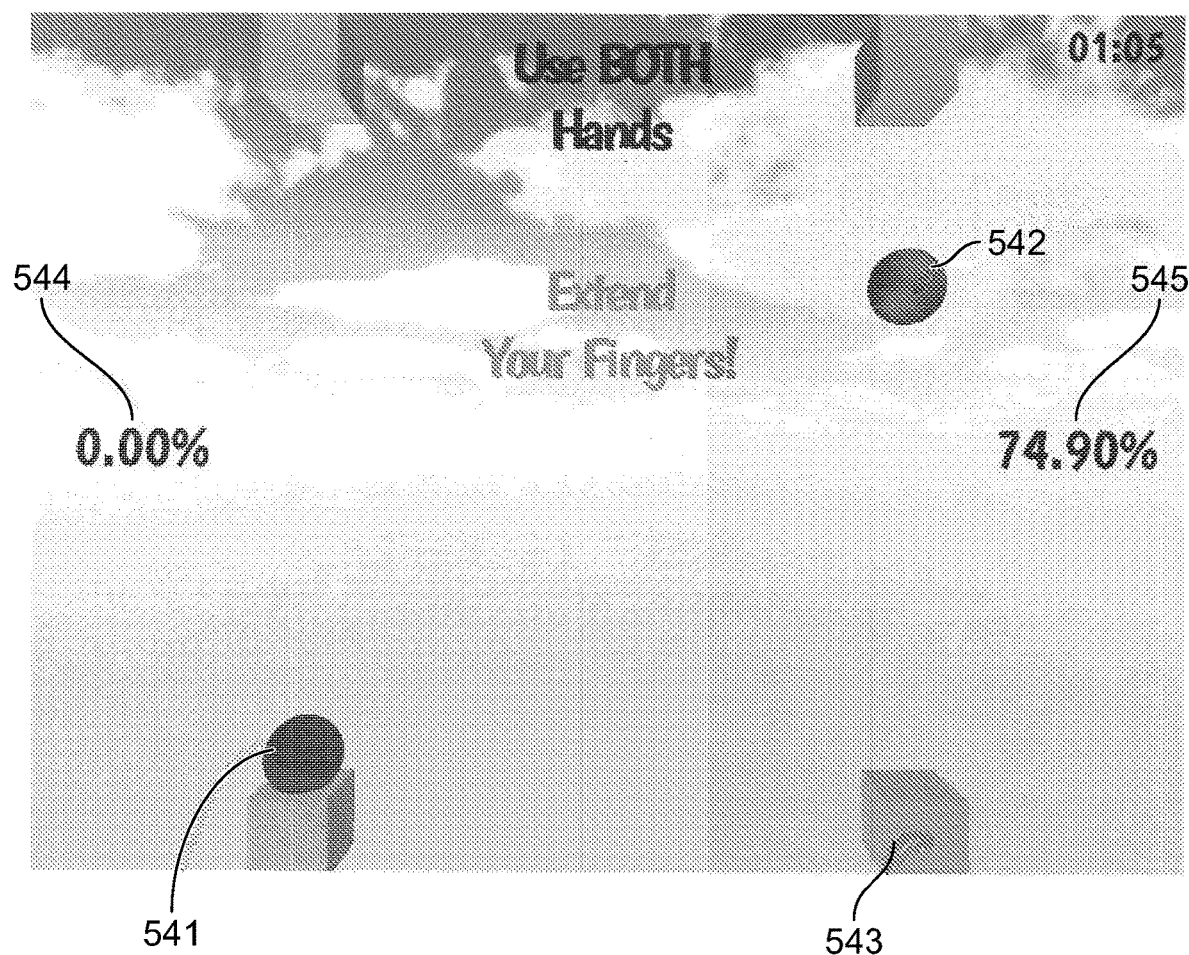
FIG. 5g is the baseline for the finger extension detected by the rotating lever

Certain patients 4 may have difficulty extending fingers 171, so a finger extension baseline 540 is used to measure their ability to open hand 17 (FIG. 5g). Baseline 540 measures the range of extension movement of fingers 171 of each hand 17. In one embodiment, unlike the range baselines 41 and 42, done in sequence, the finger extension baseline 540 is done simultaneously for both hands 17. As seen in FIG. 5g, patient 4 sees two spheres 541, 542 that move vertically between target blocks 543, in proportion with the fingers 171 extension movement. Patient 4 is first instructed to keep fingers 171 flexed, and balls 541, 542 move down to blocks 543. This represents 0% extension as seen in percentage 544. Subsequently patient 4 is instructed to open (extend) fingers 171 as much as possible, which corresponds to another percentage 545. In FIG. 5g the finger extension baseline 540 shows hand-specific percentages 544, 545 of full motion. When patient 4 extends fingers 171 the balls 542 move up. For spastic patients 4 fingers 171 will have substantial difficulty extending. The resulting limited range for the paretic hand 17, and full range of the non-paretic one are then mapped differently to hand avatars 19. The two hand avatars 19 will thus show full fingers extension during games 1.

Figure 5H:
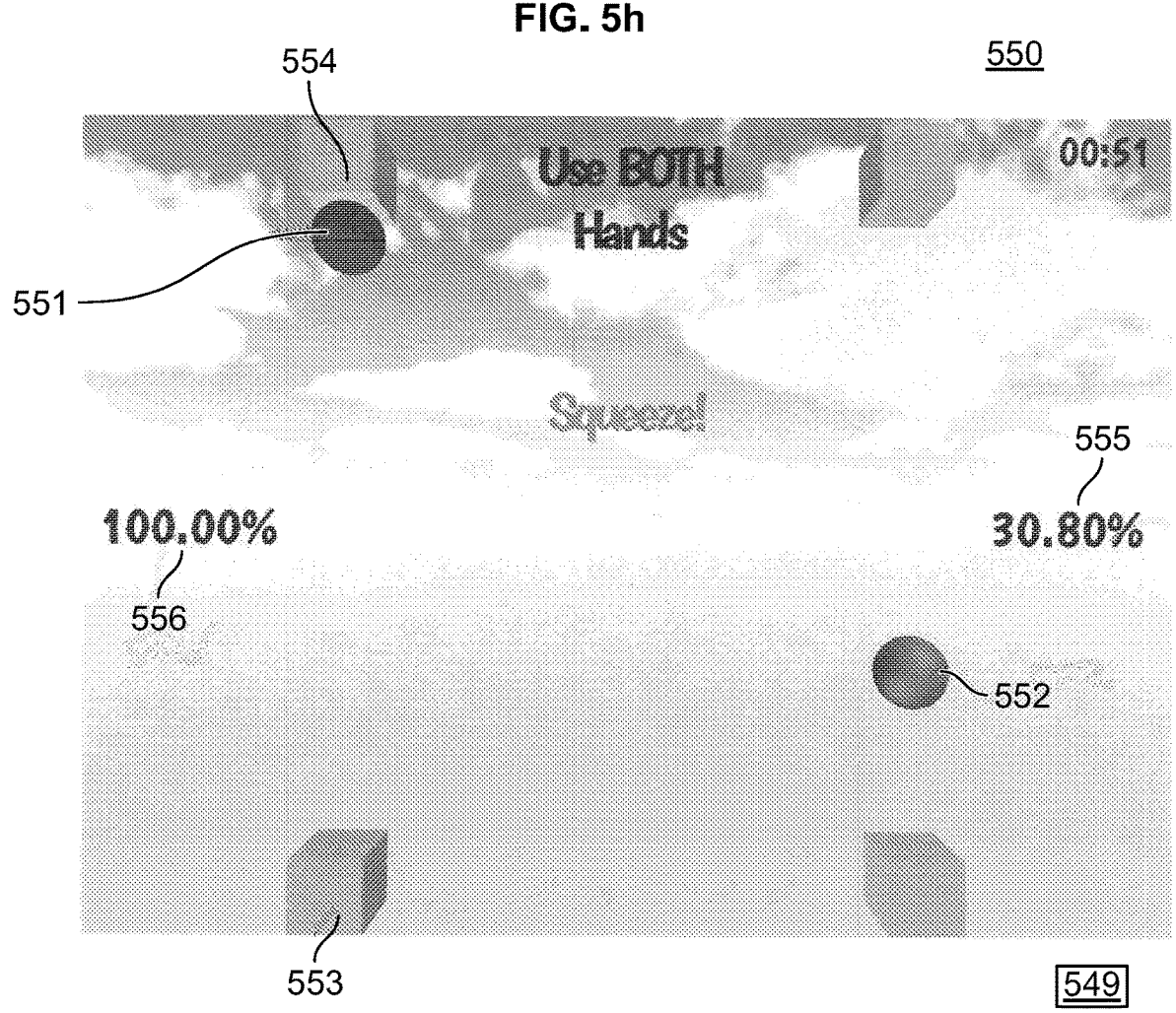
FIG. 5h is the baseline for hand grasping of the deformable element.

In one embodiment, game controller 11 is modified to add the ability to measure patient 4 grasping force 549. In this embodiment, a grasping baseline 550 is used (FIG. 5h). Similar with finger extension baseline 540 (FIG. 5g), grasping force baseline 550 may be done simultaneously for both hands 17. As illustrated in FIG. 5h, patient 4 sees two spheres 551, 552 that move vertically between target blocks 553, 554 in proportion with hand 17 grasping force. Patient 4 is first instructed to keep fingers 171 flexed, but not apply any grasping force 449. In this situation balls 551, 552 move down to blocks 553. This represents 0% grasping force. Subsequently patient 4 is instructed to grasp as hard as possible, which corresponds to 100% percentage 556. In FIG. 5h grasping force baseline 550 shows hand-specific percentages 555, 556 of full grasping force. Patients 4 with weak hands 17, will have substantial difficulty applying or maintaining a large grasping force 449. The resulting limitation leads to adaptation of games 1. Namely a fraction of maximal grasping force 449 is required in games 1, such to avoid patient 4 fatigue. This percentage of maximal grasping force 449 is specific to each hand 17.

Games to Train Focusing

Figure 6A:
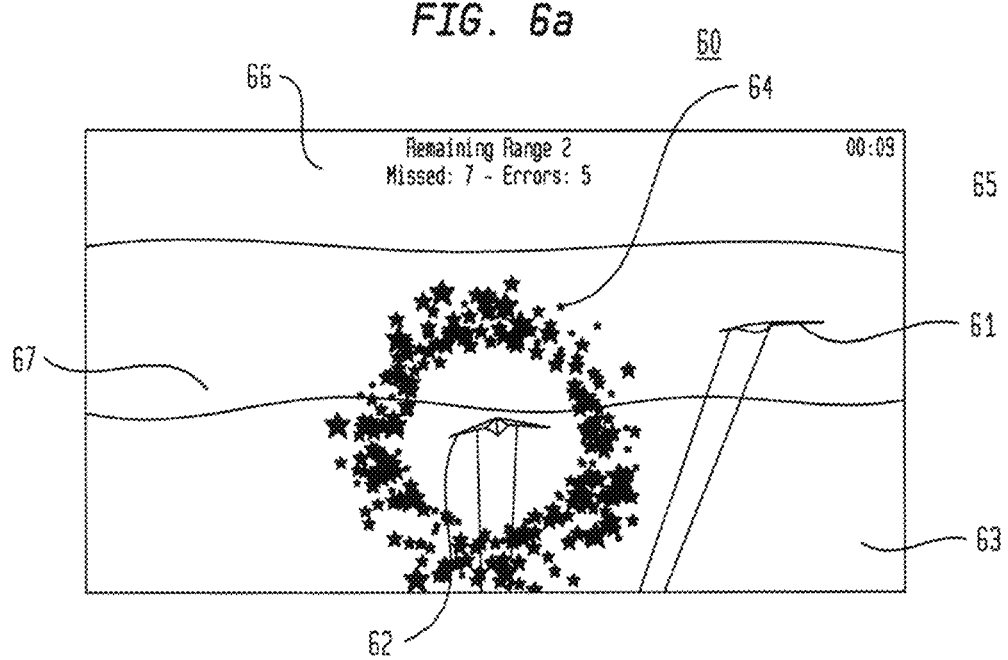
FIG. 6a illustrates a Kite game to train focusing.
Figure 6B:
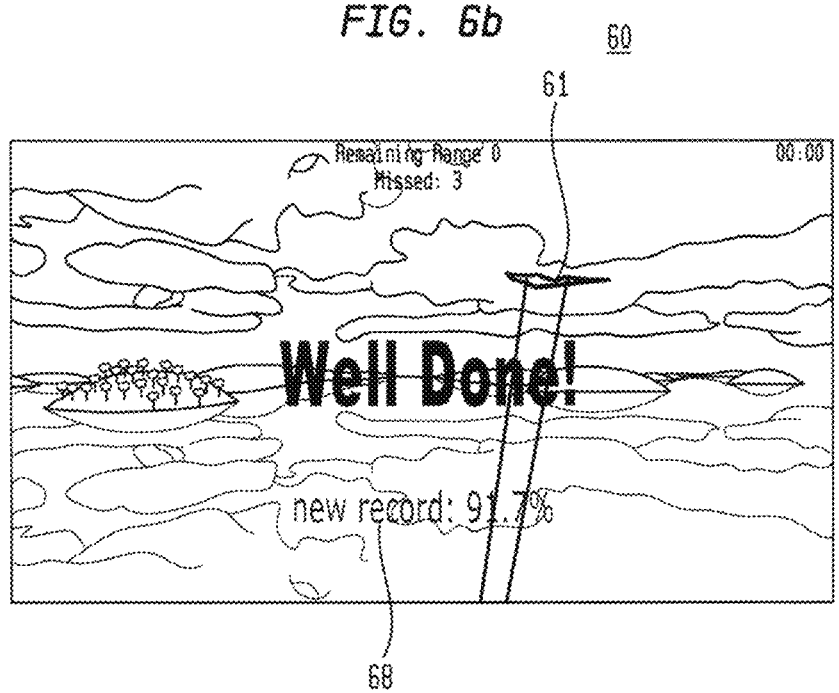
FIG. 6b illustrates a Kite game summative performance feedback.

Two games were developed to train patient's 4 ability to focus. The Kites game 60 presents two kites 61, 62 flying over water 63, while the sound of wind is heard (FIG. 6*a*). One kite is green, one red, and they have to be piloted through like-colored target circles 64, 65. The circles 64,65 alternate randomly in their color and their position on the screen, and the difficulty of the game 60 is modulated by the speed of the circles 64, 65, the duration of the game 60, the visibility 66 (a foggy sky gives less time to react) and the presence of air turbulence (acting as a disturbance 67). The game 60 calculates the percentage 68 of targets entered vs. those available, and displays it at the end of the game 60 as summative feedback on performance (G. 6*b*).

The Kites game 60 has a score to objectively measure patient's 4 performance:

$$\text{Success } \% * s_{kite} * f_r * \left(\frac{100}{100 - d_f}\right) * (1.2 \text{ if bimanual})$$

In this game, the success rate, given by the percentage of rings caught 68, is multiplied by the redefined parameters, kite 61 speed ($s_{kite}$) and ring 64 frequency ($f_r$=number of rings per unit time), as each parameter works to increase the difficulty of the game 60. The term in parentheses considers the fog density ($d_f$), applying a higher multiplier for denser fog 66. Since all parameters other than success rate are predefined at the start of the game 60, the final score is directly proportional to the number of rings 64 hit. Finally, a 20% bonus is granted for bimanual mode so to account for increased difficulty that introduces new sources of error (hitting the ring 64 with the wrong kite 61).

Figure 7A:
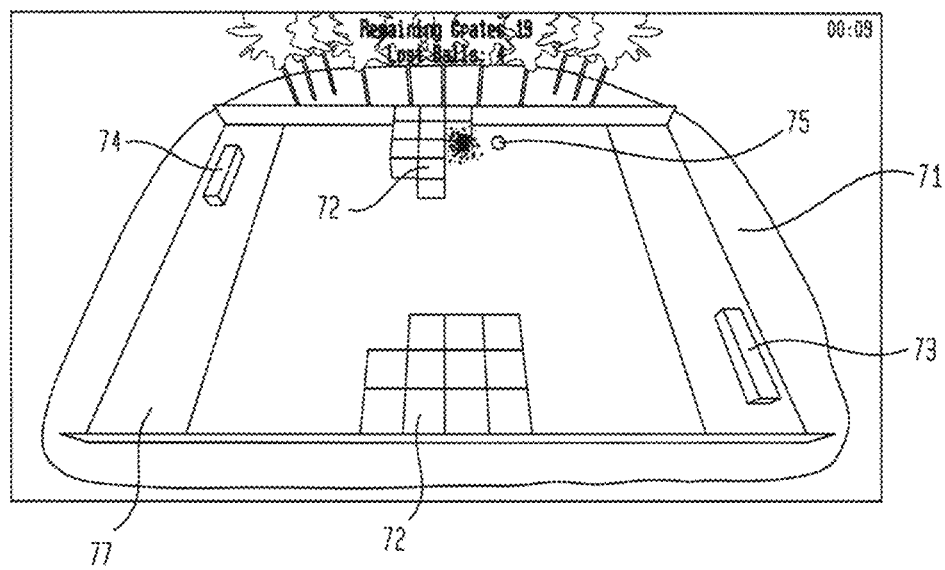
FIG. 7a illustrates a Breakout 3D game in bimanual mode which trains split attention and dual tasking in an orientation corresponding to predominantly in-out arm movement.

The Breakout 3D game 70 is a bimanual adaptation of the game developed earlier by this group for uni-manual training on the Rutgers Arm system. See Reference 16. The scene (FIG. 7*a*) depicts an island 71 with an array of crates 72 placed in a forest clearing. Two paddle avatars 73, 74 of different color, each controlled by one of the patient's hands 17 are located on each side of the crates 72. The patient 4 needs to bounce a ball 75 with either paddle 73, 74, so to keep it in play, and attempt to destroy all the crates 72. The ball 75 is allowed to bounce off several crates, destroying one crate 72 at each bounce. This is the preferred implementation when cognitive training is the primary focus of the game 70. If motor retraining is the primary focus of the game (such as for patients 4 post-stroke) then the ball 75 is allowed to destroy only one crate 72 after each bounce off the paddle avatar 73 or 74. This insures increase arm 22 movement demands corresponding to a given number of crates 72 to be destroyed. The sound of waves is added to help the patient 4 relax. The difficulty of the game 70 is modulated by the speed of the ball 75, the size of the paddles 73, 74, and the number of crates 72 to be destroyed in the allowed amount of time.

Figure 7B:
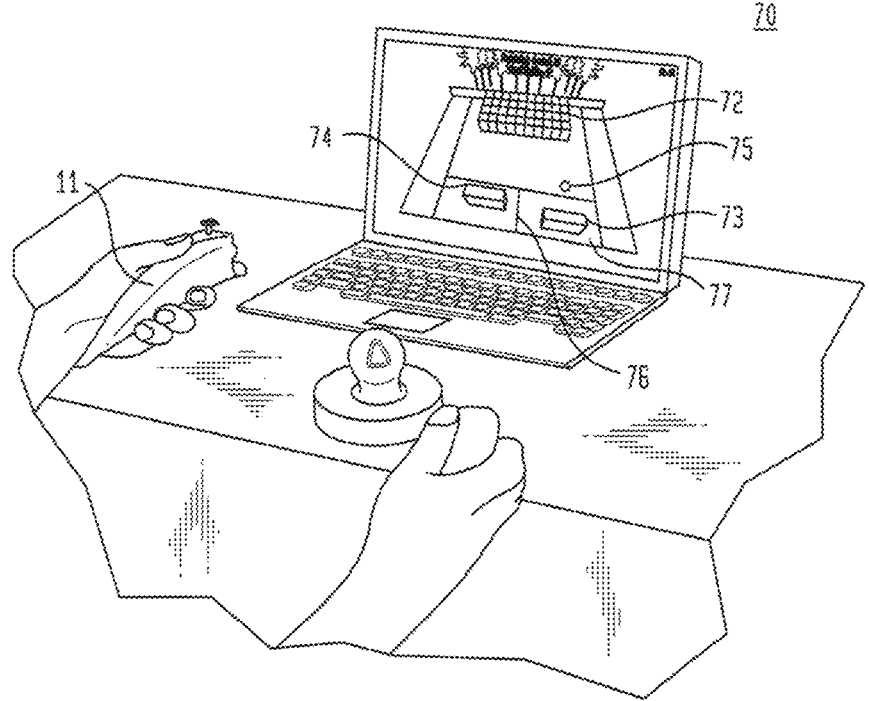
FIG. 7b illustrates Breakout 3D game in bimanual mode which trains split attention and dual tasking in an orientation corresponding to predominantly left-right arm movement.

In a different version of the Breakout 3D game 70, the paddle avatars 73,74 are close to the patient 4, and the crates 72 are further away. In this version of game 70 the predominant arm 22 movement is left-right (FIG. 7*b*). In this configuration a fence 76 is located at the middle of the court 77, so to prevent one paddle avatar 73, 74 from entering the other avatar's space. This features insures that the patient 4 uses both arms 22 to play the game 70. The score for Breakout 3D is given by:

$$\text{crates hit} * \left(\frac{v_{ball}}{l_{paddle}}\right) * \left(\frac{1}{\log(\text{lost balls} + 2)}\right) \quad (2)$$

The number of points awarded for each destroyed crate 72 is dependent not only on the preset parameters Ball_speed ($v_{ball}$) and Paddle_length ($l_{paddle}$), but also on the number of balls 75 lost. Since the logarithm is an increasing function, there is always a penalty for losing balls 75. Yet, as more balls 75 are lost, the penalty increases at a progressively slower rate, enabling players 4 of lesser skill to achieve better scores. The number 2 is added to prevent divide-by-zero issues (in case no balls 75 were lost).

Games to Train Memory

The first memory game is Card Island, 80 (FIG. 8), again a bimanual version of the game previously used in uni-manual training on the Rutgers Arm system. The patients 4 are presented with an island 81 and an array of cards 82 placed face down on the sand 83. The array of cards 82 is divided symmetrically by a central barrier 84, such that each hand avatar 19 has to stay on its half of the island 81. When a hand avatar 19 overlaps a card 82, the patient 4 can turn it face up by squeezing the Hydra pendant trigger 13. The task is to take turns turning cards 82 face up so to find matching pairs. Since non-matching cards 82 turn face down again, the patient 4 has to remember where a given card 82 was seen before, something that trains short term visual memory. When a card 82 is turned face up, a voice utters a word associated with the image on the card 82. For example if the card 82 depicts a banana, then the word "banana" is uttered, something that trains short term auditory memory. Once a card 82 had been seen, its back changes color, which is a cognitive aide to the patient 4 playing the game. The game 80 difficulty is proportional with the number of cards 82 in the array, and the allowed length of time to find all card pairs.

Card Island is scored by:

$$\left(\text{Correct matches} - \frac{\text{Errors}}{2}\right) * \left(\frac{\text{Deck Size}}{\log(\text{Playtime})}\right) \quad (3)$$

An incorrect match deducts points equal to half of a correctly matched pair. This allows players 4 a second chance to correct their mistake. If the mistake is repeated a second time, the score for eventually hitting the correct match is nullified, and deducted from the total score. Leniency is granted towards slower players 4 as exhibited by the logarithm of their playtime measured in seconds. At the same time, this leniency is also depending on the starting deck 82 size. Lastly, no performance bonus is given for bimanual play mode, as the difficulty of this game lies in the player's 4 short-term visual memory abilities.

Figure 9A:
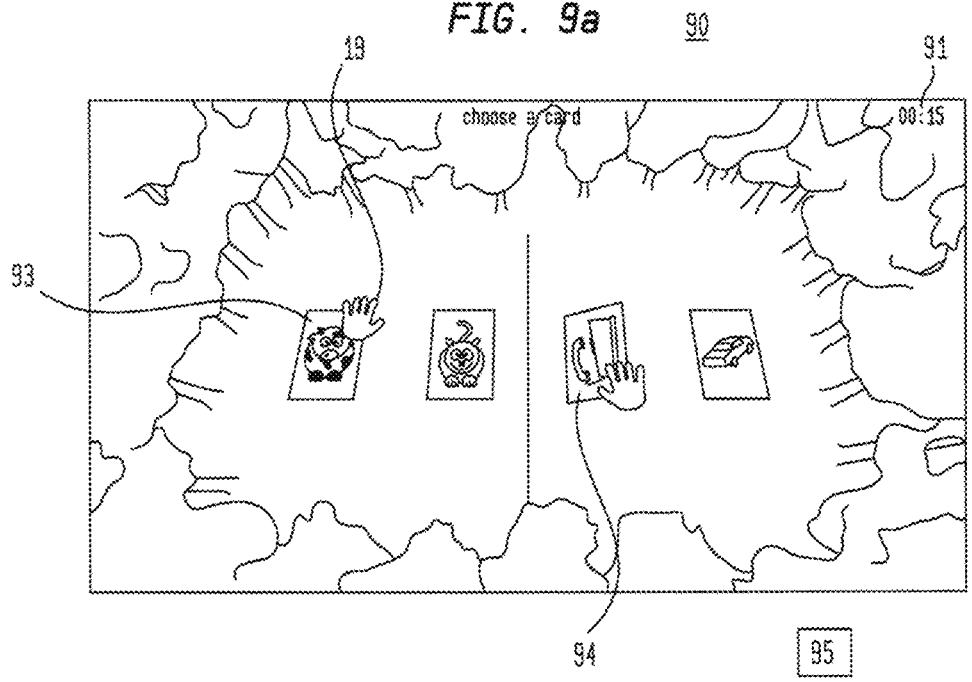
FIG. 9a illustrates a card game training long term visual and auditory memory, showing Phase 1 of the game asking the patient to choose one card and remember it for later.
Figure 9B:
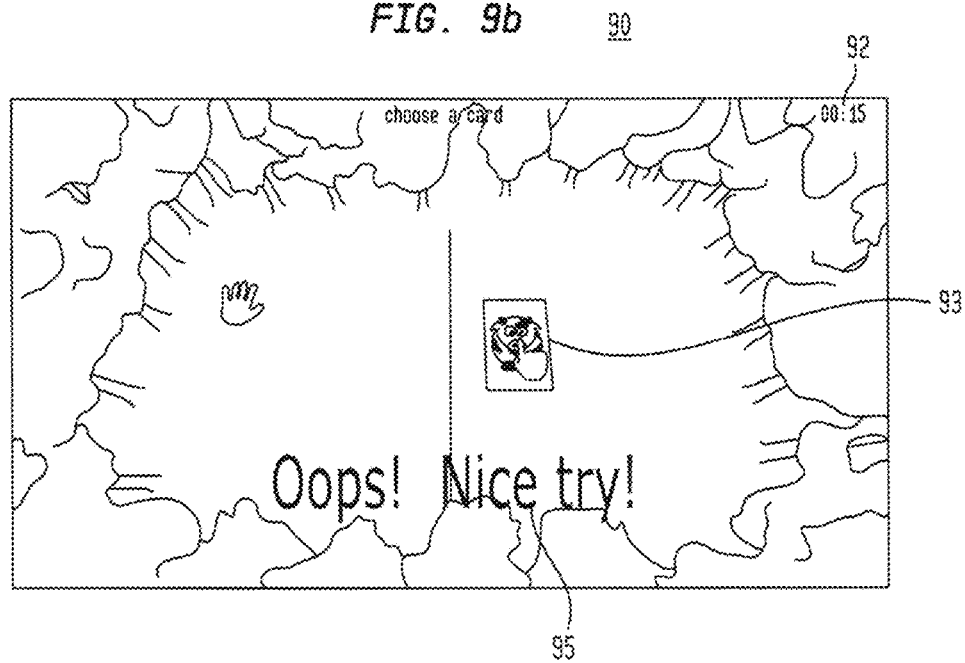
FIG. 9b illustrates a situation where, after a number of other games are played, the patient needs to recall the card initially selected.

Remember this card, 90 (FIG. 9*a*) is a game that trains long-term visual and auditory memory. The game consists of two parts 91, 92, interspaced by other games. In the first part 91 the patient 4 is presented with a number of cards 93 placed face down. Each card needs to be turned face up, at which time a sound in played associated with the image on the card. For example, if the card 93 depicts a phone booth 94, then a ring tone 95 in played. After all cards 93 had been explored, the patient 4 selects one, by flexing the hand avatar 19 over the card, and is prompted with the "Remember this card" text. After a number of other games are played, the second part of the game 92 appears, with a scene that shows the cards 93 previously explored, this time lined up face up. The patient 4 is asked to select the card he had been asked to remember before. If the attempt is unsuccessful, the "Oups, nice try!" text 95 appears (FIG. 9b), otherwise the patient 4 is congratulated for remembering correctly. The difficulty of the game 90 is modulated by the number of card choices 93, as well as the number of other games interposed between the two parts 91, 92 of this delayed recall game 90.

The score is:

$$\frac{50 * \text{Number of Cards}}{\log(\text{Recall time} + 2)} \quad (4)$$

The score scales linearly with the number of cards 93 while being more lenient on the time taken to recall and choose the correct card. The recall time is the time taken by the patient 4 to pick their previously selected card among those shown, measured in seconds. For any given number of cards 93 in this formula, a player 4 who takes less time to choose the correct card will always receive a higher score than a slower player. However, the slower players will not see a larger gap in scores, regardless of how long they take to remember the original card. Again, 2 (measured in seconds) is added to the recall time in order to prevent divide-by-zero errors.

Game to Train Executive Function

Towers of Hanoi 3D game, 110 is similar to the version of the game being played with a mouse online. The patient 4 has to restack a pile of disks 111 of different diameters, from one pole 112 to another pole 113, using a third pole 114 as way-point. The game 110 trains decision making/problem solving by setting the condition that no disk 111 can be placed on top of a smaller diameter one.

Figure 10:
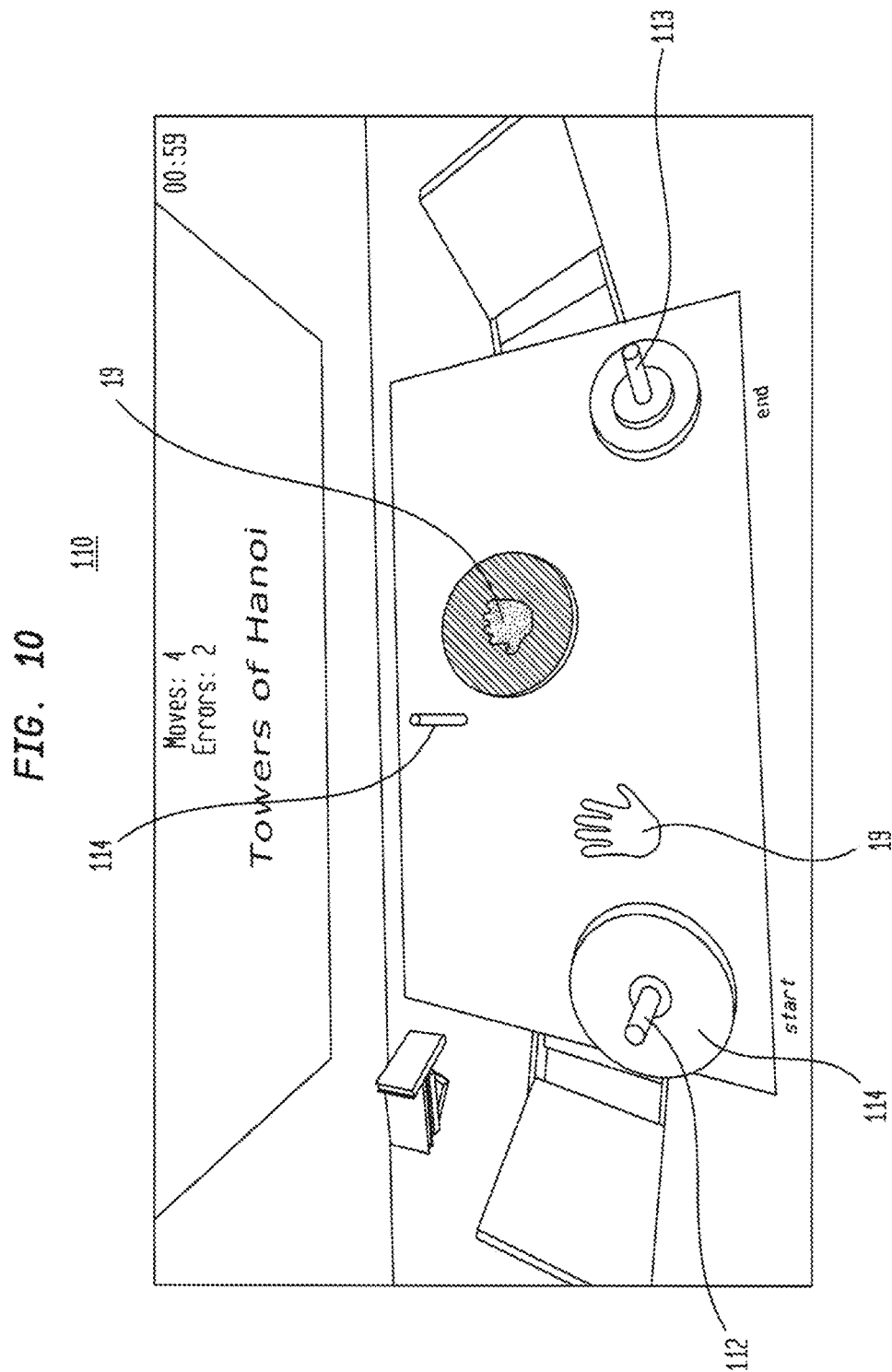
FIG. 10 illustrates the use of the Towers of Hanoi 3D game to train executive function wherein two hand avatars are allowed to only manipulate like-colored disks.

In the version of the game 110 for bimanual therapy, the scene shows two hand avatars 19, one green and one red and similarly colored red and green disks 111 (FIG. 10). Each hand avatar 19 is allowed to manipulate only disks 111 of similar color. The game 110 chooses randomly the green or the red color for the smallest disk and allocates the other color to the other disks. In this configuration, both hands 17 are doing approximately the same number of moves. The difficulty of the game 110 depends on the number of disks 111 (2—easy, 3—medium, 4—difficult). The number of moves in the game 110 is counted and compared to the ideal (smallest) number of moves to complete the task. Thus cognitively, achieving an economical (minimal) number of moves to solve the problem is indicative of good problem solving skills.

The score is:

$$\frac{150 * \text{disks} * (1.2 \text{ if bimanual})}{\log(\text{moves} - pow(2, \text{disks}) + 3) * \log(\text{Playtime})} \quad (5)$$

If a patient 4 was unable to complete the game 110, we assign a flat score of 100, so to maintain patient 4 motivation. In this game, each disk 111 is worth 150 points, with 20% increase in bimanual play mode to account for the increased difficulty and newly introduced sources of error. This number is countered by a product of logarithms (for leniency): the first compares the number of moves made by the patient 4 against the optimal solution, and the second factors in the time taken to solve the task.

Dual Tasking and Therapy Gradation

As stated before, dual tasking is typically problematic with older populations (whether stroke survivors or not). Thus some of the games have embedded dual-tasking features, notably Breakout 3D 70. When the dual tasking parameter is set, the paddle avatar 73, 74 characteristics depend on whether the trigger 13 is squeezed during movement or not. When a momentary squeeze is required, the patient 4 has to squeeze the trigger 13 at the moment of bounce, lest the ball 75 passes through the paddle 73, or 74 and is lost. When a sustained grasp is required, the movement of the paddle 73, 74 is decoupled from that of the pendant 11 when the trigger 13 is not squeezed. Thus the patient 4 has to remember to keep squeezing to move the paddle 73, 74 to bounce the ball 75. Recognizing that sustained squeezing may be fatiguing and may induce discomfort for some patients 4, the game 70 sets a threshold as a % of range when classifying an index 18 flexion as a squeeze. This threshold is based on the finger 18 flexion baseline 40 previously described.

Naturally, the introduction of the squeezing (grasping) requirement further increases game 70 difficulty. Thus the weeks of therapy are gradated in terms of session duration and game difficulty. The approach in this application is to begin with shorter sessions of 30 minutes in week 1, progress to 40 minutes in week 2 and 50 minutes for the remaining weeks. The games in week 1 are uni-manual and played with the non-paretic arm 22, so to familiarize the patient 4 with the system 100 and its games 1. Gradually the games 1 difficulty is increased, switching to bimanual mode in week 2 or later, and in the last 3 weeks the dual tasking condition is introduced. The aim is to always challenge the patient 4, offer variety, but make games 1 winnable, so to keep motivation high.

Arm 22 and Index 18 Repetitions 120

It is known in the art that the amount of movement repetitions 120 within a task is crucial to induce brain plasticity. Within the system 100 described here the tasks are dictated by the different games 1, and the system 100 measures the number of repetitions 120 during play, The number of repetitions 120 is arm specific, as well as index finger 18 specific (right, left), and is summed for the session. The amount of repetitions 120 is an indication of the intensity of play, and a useful tool for the therapist.

Figure 11:
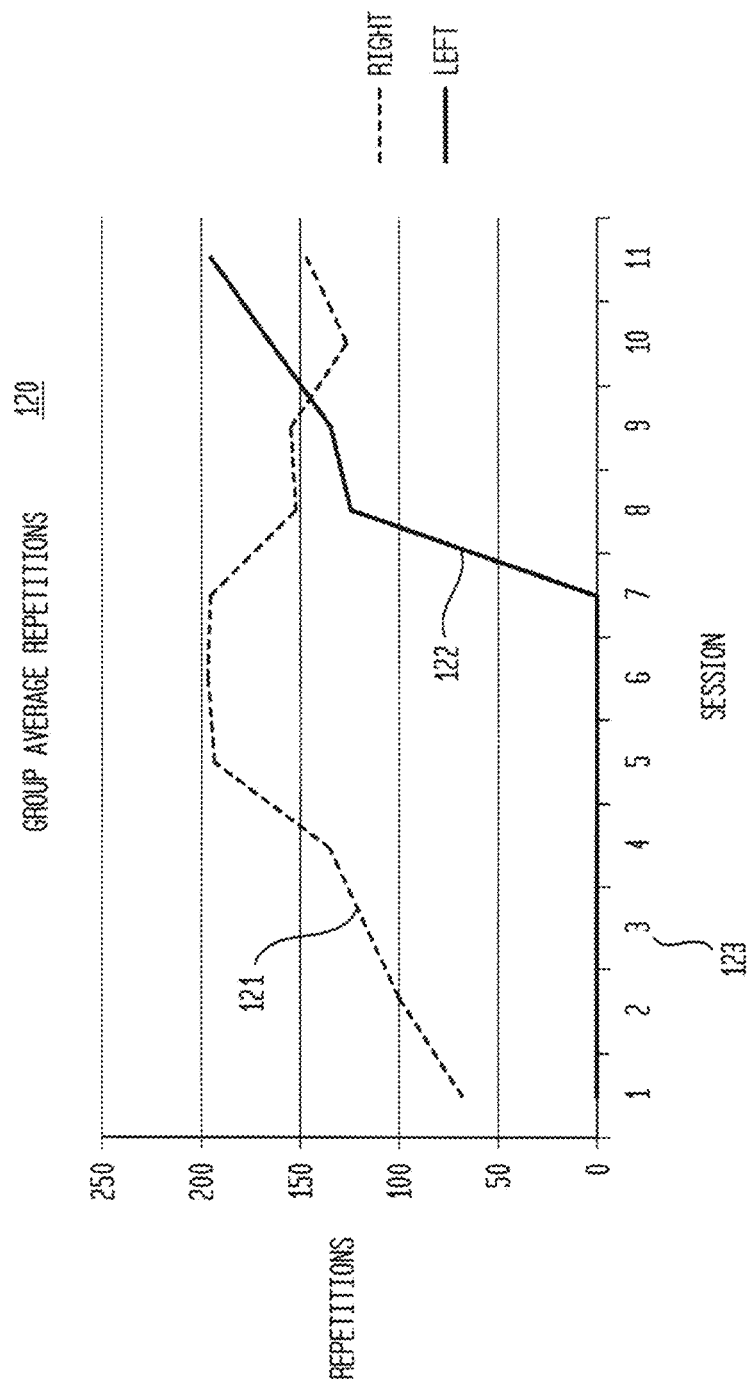
FIG. 11 shows a graph depicting average right and left arm repetitions during group training over a sequence of sessions.

In group therapy the repetitions 120 may be averaged over the group of patients 4 for a given session. FIG. 11 depicts a graph showing the left and right arm 22 number of repetitions 121, 122 over a sequence of sessions 123. It can be seen that over the first 7 sessions the right arm number of repetitions 121 grows, while the left arm 22 is motionless. This is due to the fact that during these 7 sessions the games 1 were played in uni-manual mode, and thus only the right arm was used. The reason the number of repetitions 121 increases for right arm 22 is the increased session duration, implying more games played. Once the games 1 started being played with both arms 22, it can be seen that the left arm 22 has a steep increase in its number of movement repetitions 122, while the right arm number of repetitions 121 is somewhat reduced. Eventually both arms share about equally in the game play.

Discussion

A pilot feasibility study took place with two elderly participants who were in the chronic phase of stroke and had arm/hand spasticity (See Reference 17). A short video can be submitted to show one of participants during therapy.

The feasibility study aim was to determine technology acceptance as well as any clinical benefits in the cognitive and emotive domain. These were measured by a blinded neuro-psychologist consultant using standardized tests. Results showed excellent technology acceptance and benefits to the two patients 4 in various cognitive domains. One patient had reduced depression following the therapy.

Subsequently a larger study with 10 elderly nursing home residents took place in summer 2013. See reference 18. Eight of the patients 4 had dementia and one had severe traumatic brain injury. They played the games described above and three other games we developed. The new games were: Pick-and-Place bimanual 130, Xylophone bimanual 140, and Musical Drums 150, bimanual.

Figure 12:
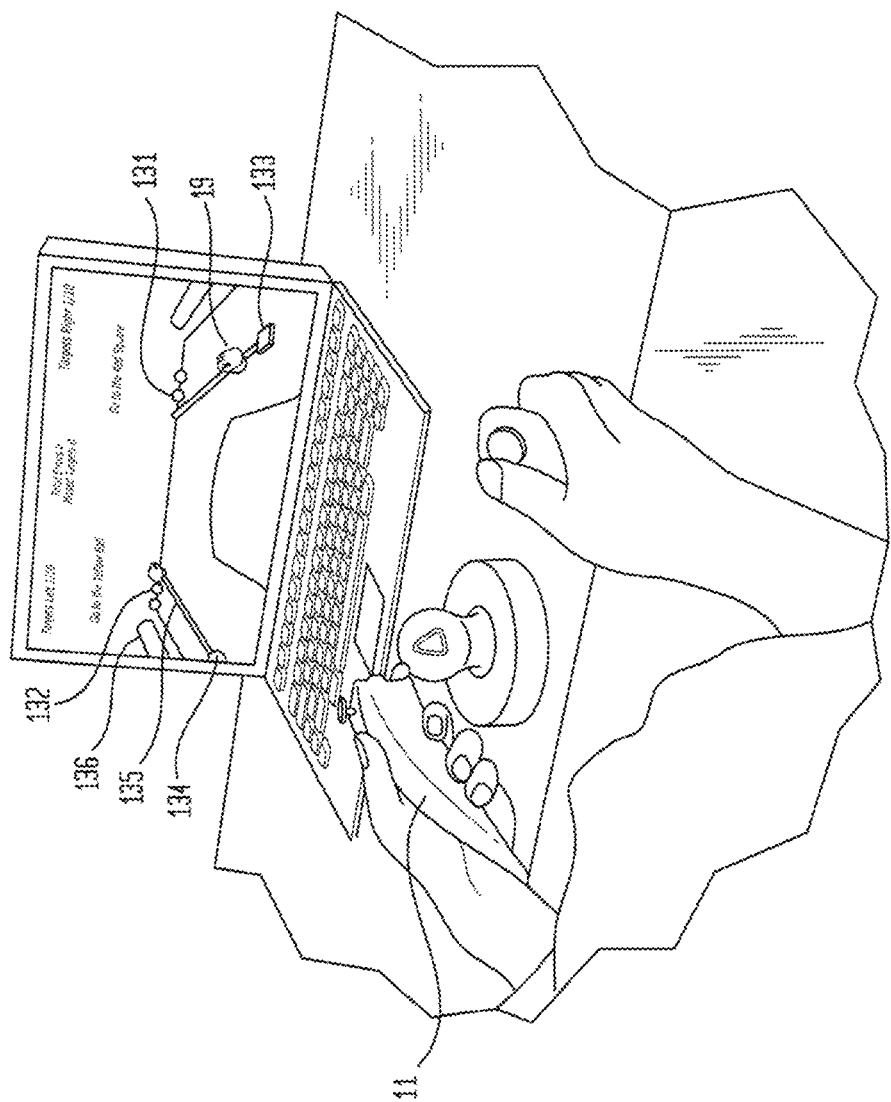
FIG. 12 illustrates a Pick-and-Place bimanual game.

The Pick-and-Place game 130 bimanual (FIG. 12) shows two hand avatars 19 that need to pick a ball 136 each from three possible choices 131, 132 and move them to target areas 133, 134 following prescribed (ideal) paths 135. Each time a ball 136 is correctly moved to a target 133, 134, a different sound is played. The patient 4 has a choice of moving one ball at a time or of moving both arms 22 at the same time (a more difficult task). The game 130 difficulty depends on the number of required repetitions, and errors are counted whenever the wrong ball is picked up. The Pick-and-Place game trains hand-eye coordination and dual tasking may be introduced by requiring the patient to squeeze the Hydra trigger 13 to keep the ball 136 grasped by avatar 19.

Figure 13:
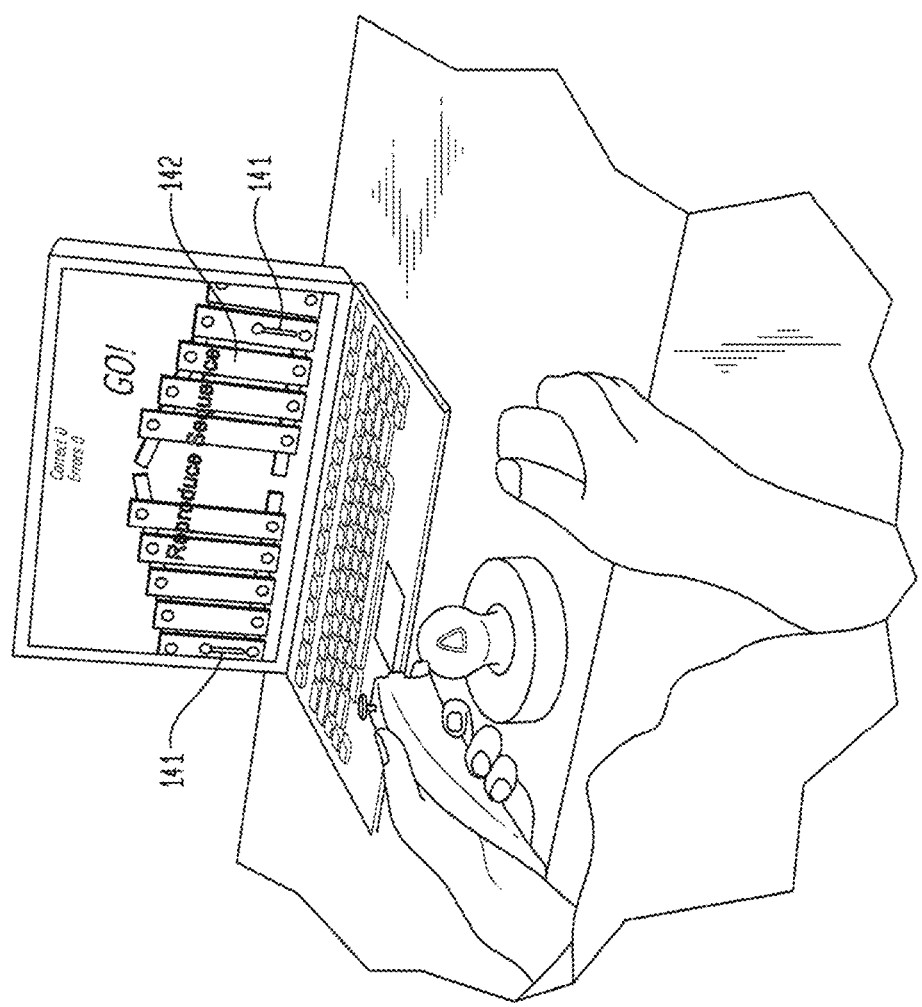
FIG. 13 illustrates a Xylophone bimanual game.

In the Xylophone game 140 (FIG. 13) the patient 4 controls two hammer avatars 141, and needs to hit keys 142 to create a sound (play a note). The patient 4 is tasked with reproducing sequences of notes by playing the instrument keys 142 in the correct order. The difficulty of the game depends on the length of note sequences to be reproduced, as well as the total amount of time available to complete a series of note sequences.

Another game is Musical Drums 150 (FIG. 14a) where the patient 4 needs to hit notes 151 scrolling on the screen when they overlap a drum 152 to get points. The difficulty of the game 150 increases with the tempo of the song 153 being played, corresponding to faster scrolling of the notes 151 across the screen. Further increase in difficulty occurs when notes scroll across more drums 152.

Figure 14B:
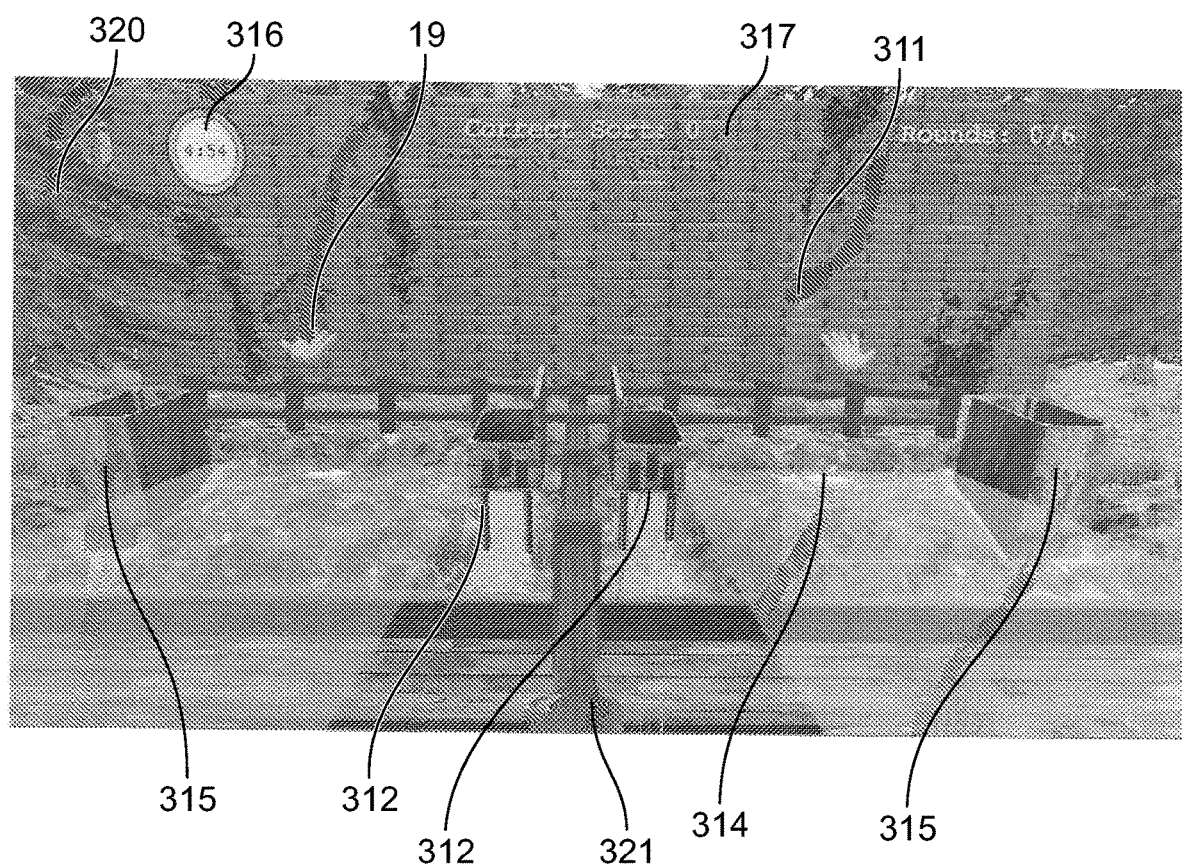
FIG. 14b illustrates a Catch 3D bimanual game.

FIG. 14b depicts a Catch 3-D game 310 developed subsequently, which, in one embodiment, is played with the therapeutic game controller 160 (FIG. 15) rather than the general purpose game controller 11. In one embodiment, game 310 is played in bimanual mode and patient's hands 17 control two hand avatars 19, which are tasked with catching falling objects 311 of various shapes and colors. Patient 4 is asked to sort caught objects 311 based on color and shape and deposit them in bins 312 which depict matching objects 313 on their side. If falling objects 311 do not match corresponding objects 313 shown on sorting bins 312, then patient 4 needs to deposit the falling objects 311 in garbage bins 315. Two garbage bins 315 may be located on either side of divider 321. Divider 321 prevents hand avatars 19 from crossing to the other side of the scene. Divider 321 thus prevents patient 4 from over using one arm 26 versus the other arm 26. This feature combats what is known in the art as "learned nonuse," typical of stroke survivors affected on one side of the body (Reference 19). At higher level of difficulty a wind effect 319 is simulated by pushing falling objects 311 laterally. A marker 314 is provided to help patient 4 better gauge where the object 311 is going to land thus overcoming disturbances provided by the wind effect 319. Arrows 318 are indicative of wind direction and number of arrows are indicative of wind intensity (1 to 3 arrows, for example). A clock 316 placed on a background wall 317 provides information on the remaining game duration. Vegetation 320 is meant as a visual distractor, with higher levels of difficulty of game Catch-3D 310 having more vegetation 320.

Figure 14C:
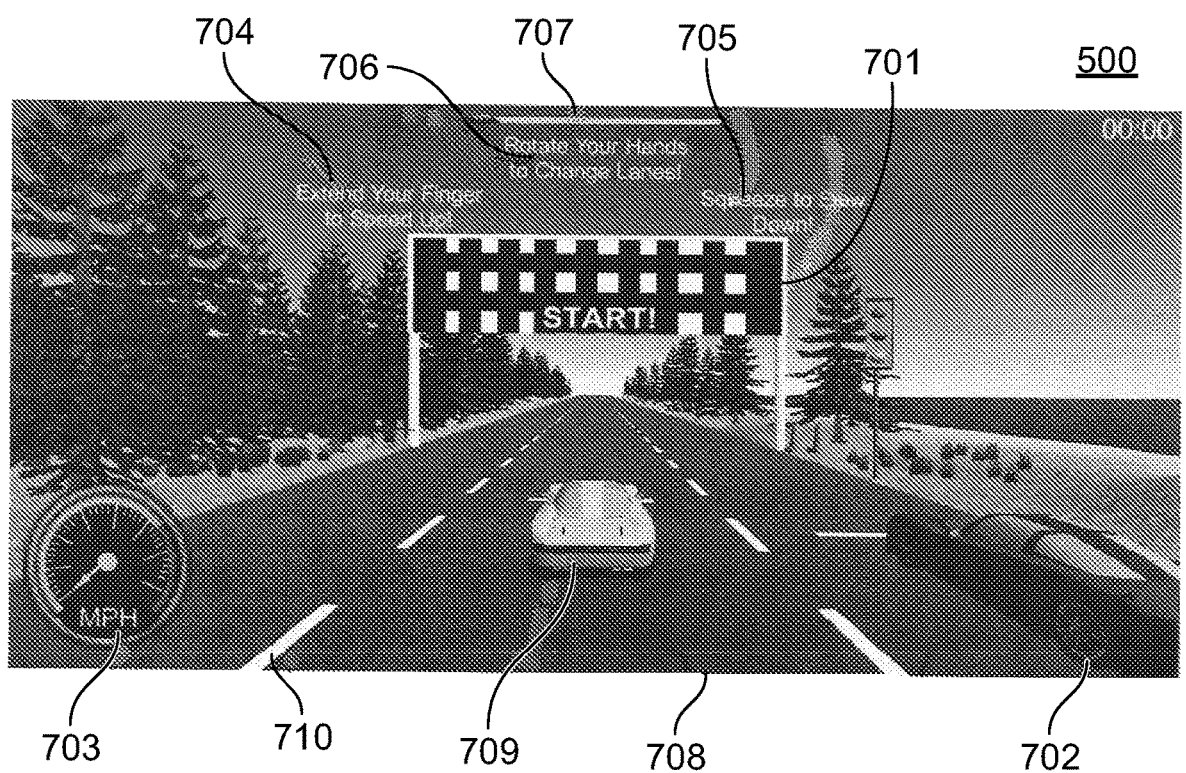
FIG. 14c illustrates Car Race bimanual game to train finger extension, grasping and pronation/supination.

FIG. 14c depicts Car Race game 700 which, in one embodiment, may be played with therapeutic game controller 160 (FIG. 15) rather than general purpose game controller 11. Game 700 depicts a car race where patient 4 controls car avatar 709, and computer 191 shows game 700 scene on display 500. Computer 191 also controls one or several opponent cars 702, presented initially at starting line 701. In one embodiment patient 4 interacts with avatar 709 using one or two therapeutic game controller 161. Car avatar 709 is able to change lanes 710 based on forearm 26 pronation/supination movement. Car avatar 709 is also able to accelerate and brake. It is envisioned that when game 700 is played uni-manually, braking is controlled by the degree of squeezing on a deformable element 166 of controller 160. It is further envisioned that car avatar 709 acceleration is controlled by the extension of patient 4 fingers 171 pressing against the mechanical lever 170 of the same therapeutic game controller 160. When patient 4 plays game 700 bimanually, one hand 17 does the braking, and the other hand 17 does the acceleration of car avatar 709. Speedometer 703 displays current speed of car avatar 709, while amount of racetrack 711 completed is visualized by racetrack gauge 707. In one embodiment racetrack gauge 707 is a straight line, with small scale version of car avatar 709 separating two portions (completed and to be completed) of race track 711. In starting scene 701, patient 4 is instructed how to control car avatar 709 through texts 704, 705, 706. Game 700 may contain a multitude of opponent cars 702, sometimes blocking passage or moving slower than car avatar 709. Therefore, winning the game requires patient 4 to combine finger 171 extension (for acceleration), grasping of deformable element 166 (for braking), and changing lanes 710 through forearm 26 pronation/supination movement. At higher levels of difficulty of game 700, there can be more opponents 702, longer game duration (longer tracks 708), and wet track 708, so to train improved arm motor control to keep car avatar 709 on track 708.

Tests required patients to play the games two times per week for 8 weeks. To measure clinical benefit, tests were done by a blinded neuropsychologist before and after the 8 weeks of therapy. These tests showed statistically significant group improvement in decision making capacity, and borderline significant reduction in depression.

In summary, one aspect of the present disclosure is to provide a method of providing therapy to a patient having a first arm, a first hand, a second arm and a second hand. The method includes executing a video game on a computer and portraying action from the video game on a display, the action being viewable by the patient; the patient holding a first component of a game controller in the first hand and manipulating an interface on the first component of the game controller with the first hand and moving the first component of the game controller with the first hand and the first arm to control the video game; the patient holding a second component of a game controller in the second hand and manipulating an interface on the second component of the game controller with the second hand and moving the second component of the game controller with the second hand and the second arm to control the video game. The first component of the game controller is separate from the second component of the game controller and can be moved independently from the second component of the game controller. The game controller sends one or more signals representative of a position of the interface on the first component, of a position of the interface on the second component, of a motion of the first component and of a motion of the second component are reported by the game controller to the computer; and the computer analyzes the one or more signals and controlling the video game to control action portrayed on the display.

The video game can also control the computer to cause a displayed object to include one of two codes wherein a first code indicates that the displayed object can be moved with the first component of the controller and a second code indicates that the displayed object can be moved with the second component of the controller. Preferably, the two codes are different colors.

While the game is played the computer monitors and stores a set of information from the first component and the second component of the controller. The set of information includes: activation of the interface (button and trigger) on the first component of the controller, movement of the first component of the controller; activation of the interface on the second component of the controller and movement of the second component of the controller.

The computer controls the video game and resulting action on the display in accordance with the set of information. The computer also analyzes the set of information to determine progress of the patient. In one embodiment, the computer controls the action displayed such that the action caused by the first component of the controller is the same as the action caused by the second component of the controller even if one of the arms does not perform as well. As explained before, extra oxygen can be fed to the patient from an oxygen tank while the patient manipulates the first component and the second component. Also as explained before the patient can wear wrist weights on the first arm, on the second arm or on both arms while the patient manipulates the first component and the second component. Alternatively, weights can be added to either the first component of the game controller, to the second component of the game controller or to both. The handheld components can be modified to have the weights attached to them.

In accordance with one embodiment, the computer controls a videogame avatar object in response to activation of the interface (button and/or trigger) on each of the handheld components of the controller. The avatar object can be controlled by movement of each handheld component of the controller. Alternatively, one avatar object can be controlled by the movement of the first (say the left) handheld component while another avatar object can be controlled by the movement of the second (say the right) handheld component. Thus, a computer can control a videogame avatar object to respond to movement of the first component of the controller if the button or the trigger on the first component are pressed and the computer controls another video game avatar object to respond to movement of the second component of the controller if the button or the trigger on the second component are pressed.

A system of providing therapy to a patient having a first arm, a first hand, a second arm and a second hand, is also provided as explained above.

Figure 15:
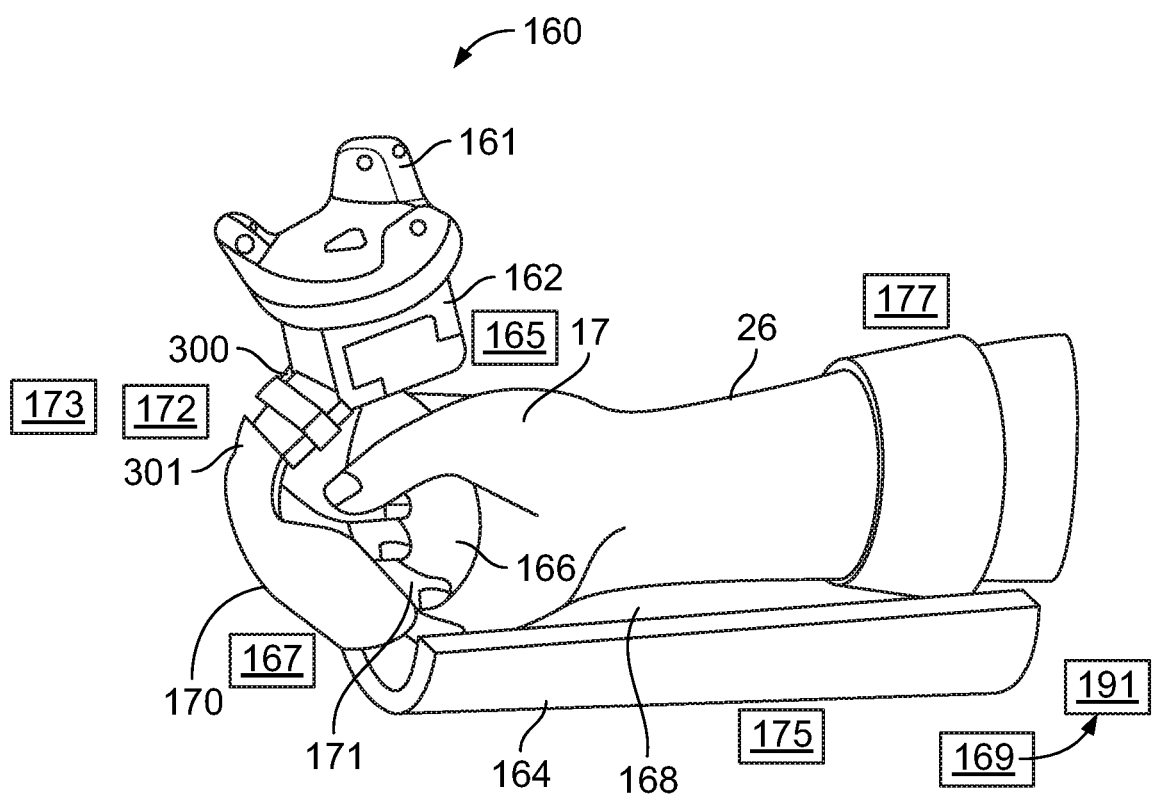
FIG. 15 illustrates a therapeutic game controller according to an embodiment.

In one embodiment, general-purpose bimanual game controller 9 is replaced by a therapeutic game controller 160 that can be integrated in therapy system 100 previously described. FIG. 15 depicts one embodiment of a therapeutic game controller 160 (also referred to as a hand-held controller). In one embodiment, system 100 will use a pair of such therapeutic game controllers 160.

Therapeutic game controller 160 detects movement of patient's hand 17 and forearm 26. Movement is detected by a plurality of sensors including 3D tracker 161, which, in one embodiment, measures the position and orientation of patient's hand 17 in real time. It is appreciated that tracker 161 may be a VIVE tracker such as that available on the market. Patient 4 rests forearm 26 on a forearm support 164 and wraps fingers 171 about deformable element 166. In one embodiment, deformable element comprises a sealed air chamber and a sensor for detecting a pressure inside the sealed air chamber. The deformable element can be various shapes such as bulb shaped or pear shaped. Computer in system 100 may be a laptop 7, but can alternatively be a medical grade computer 191 connected to a medical grade monitor 500. Computer 191 communicates, wired or wirelessly, with therapeutic game controllers 160 so to map 3D tracker 161 data to hand avatars 19 used in a plurality of therapeutic games 1. For example, one or more signals representative of data from one or more of a movement sensor (e.g., 3D tracker 161) deformable element 166 (also referred to as a grip sensor), and a finger extension sensor (described in detail herein) are sent to computer 191. Computer 191 analyzes the one or more signals and controls images on a display in communication with computer 191 based on the one or more signals.

Figure 16:
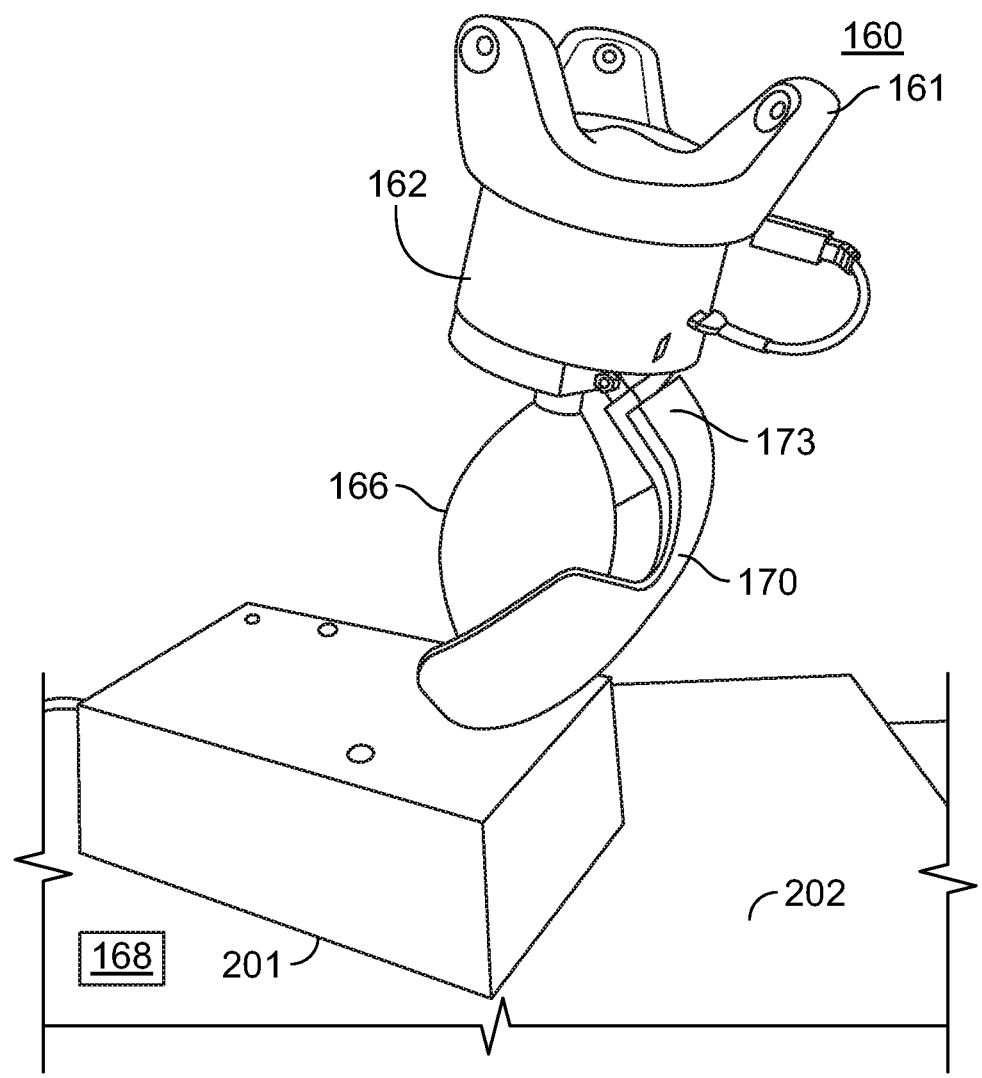
FIG. 16 illustrates a therapeutic game controller according to an embodiment.
Figure 17A:
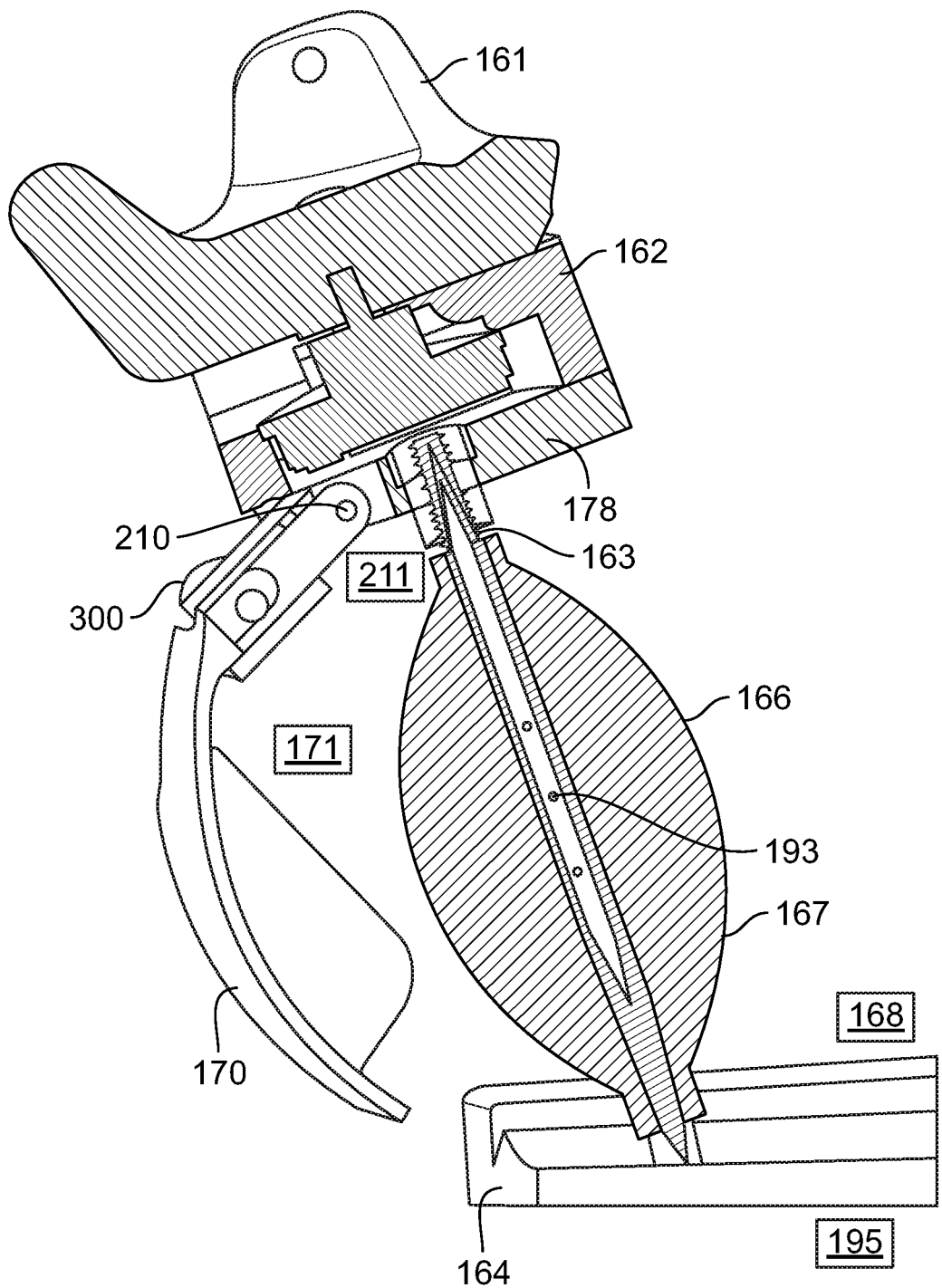
FIG. 17a illustrates a sectional view of components of the therapeutic game controller of FIGS. 15 and 16.

FIG. 16 depicts one embodiment, in which the 3D tracker 161 is rigidly attached to a support 162 which allows passage of hollow tube 163 (better seen in the therapeutic controller section shown in FIG. 17a). Tube 163 provides attachment of 3D tracker 161 to low-friction forearm support 164 and serves as conduit for wires 165 that power 3D tracker 161.

Tube 163, in one embodiment, is located inside a deformable rubber bulb or pear 166 that can be held by patient's hand 17 while patient's forearm 26 is resting on support 164. In one embodiment, two supports 164 can be used to allow training both arms 26 and hands 17 of patient 4. Tube 163-rubber pear 166 assembly, in one embodiment, is pneumatically sealed at both ends, forming air chamber 167. Tube 163, in one embodiment, has a plurality of orifices 193 in its wall. Tube 163 is connected to pressure sensor 195, which, in one embodiment, is part of the electronics 168 housed inside arm support 164. Air pressure measured by electronics 168 located inside the forearm support 164, in one embodiment, is sent to a wireless transmitter 169, and subsequently received by computer 191. When running therapeutic games 1 computer 191 detects such actions as extension of hand 17 fingers 171 pushing away mechanical lever 170, or patient's hand 17 grasping forces on deformable element 166. Computer 191 them maps such actions in real time to actions of hand avatars 19.

In one embodiment, rotating mechanical level 170 and an associated rotary sensor (together referred to as a finger extension sensor) detects extension of patient's 4 plurality of fingers 171. Mechanical lever 170, in one embodiment, is connected to tracker support 162. Furthermore, mechanical lever 171 is hinged to tracker support 162 using a rotary sensor 172, and kept slightly pressed against fingers 171 by one or a multitude of deformable springs 173. Spring constant of spring 173 is such that a light force is applied on fingers 171 by lever 170, without impeding extension of weak fingers 171. In one embodiment, the curvature of lever 170 is symmetrical, such that a single therapeutic controller 160 configuration can be used by either hand 17. In bimanual therapy, two such controllers 160 can be used. In one embodiment, the finger extension sensor comprises an adjustment mechanism that is used to adjust for a hand size of a user. In one embodiment, the adjustment mechanism comprises a mechanical wheel tightening matching arms of the finger extension sensor to those of a rotating sensor support.

FIG. 16 shows an embodiment of therapeutic game controller 160, where electronics 168 are housed in supporting box 201. In one embodiment, electronics 168 are housed in forearm support 164. In one embodiment, forearm support 164 has a curved lower surface, to minimize contact and friction with any supporting surface, such as supporting surface 202. In one embodiment, a curvature of the forearm support 164 bottom allows for forearm 26 pronation and supination movements (e.g., similar to the movement used when turning a lock).

In one embodiment, electronics 168 housed at the bottom of forearm support 164 are powered by rechargeable batteries 175, so to avoid power chords or tethers. Such tethers may impede forearm 26 natural movement, on or above supporting surface 202. In one embodiment, supporting surface 202 is a low-friction table 24.

In one embodiment, forearm support electronics 168 comprise a skin temperature sensor 176 and a pulse sensor 177. The combination of sensors 176 and 177 provides data that may be used by system 100 to determine amount of blood flow 205 to hand 17 as well as level of effort when playing games 1.

FIG. 17a depicts a sectional view of 3D tracker 161, its support 162 and pass-through tube 163. As can be seen in FIG. 17a, in one embodiment, tube 163 is threaded into plate 178, attached to 3D tracker 161 support 162. Plate 178, in one embodiment, houses the hinge of mechanical lever 170 that detects finger 171 extension. Electrical wire 165 passes through tube 163 and is connected to port 179 of 3D wireless tracker 161.

Mechanical lever 170 and plate 178, in one embodiment, are connected through a rotary joint 210 which allows rotation of lever 170 when pushed by one or a plurality of patient's 4 fingers 171. Rotary joint 210, in one embodiment, contains rotary sensor 211, which measures the rotation of lever 170.

Figure 17B:
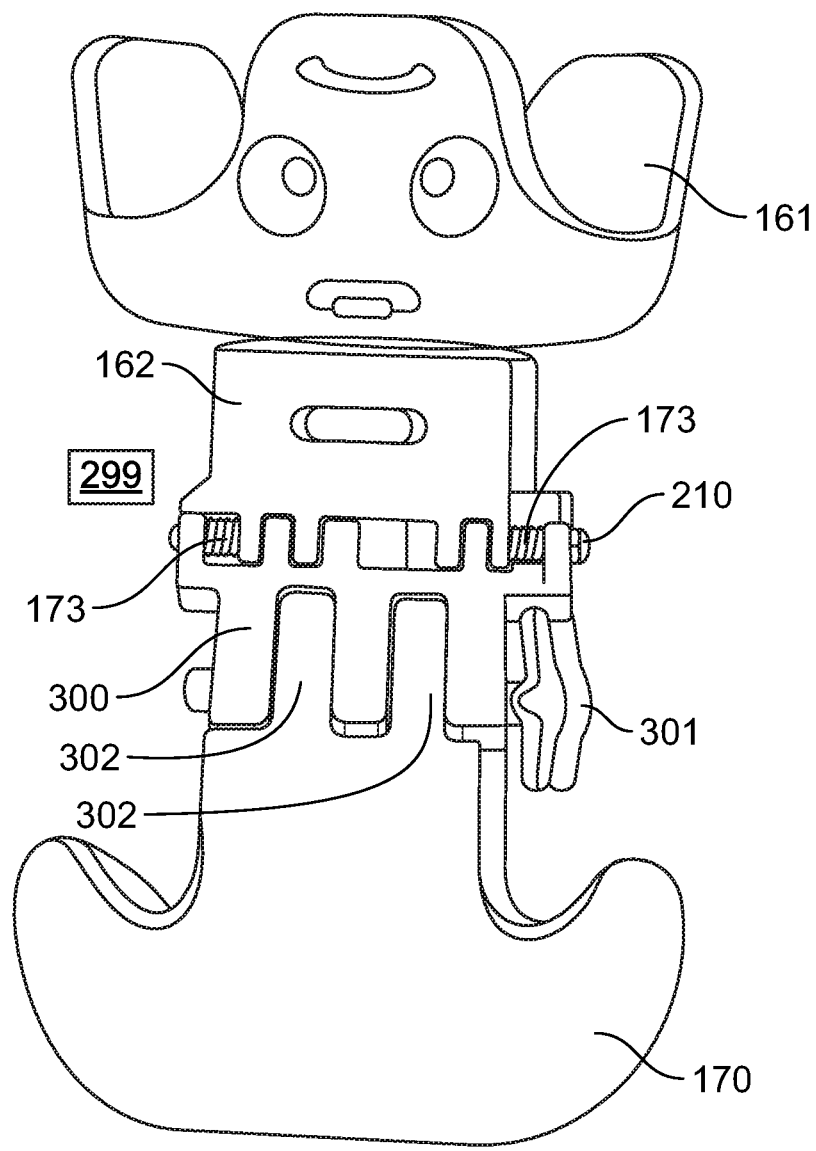
FIG. 17b is a detailed view of the mechanical lever attachment which adapts to different hand sizes.

FIG. 17b is a detail of the mechanical hinge of lever 170 modified so to adapt to different sizes of hands 17. In one embodiment, hand size adaptation is realized through translation mechanism 299 comprised of rotating element 300 which guides in-out translation of arms 302 of lever 170. The assembly contains a wheel 301 which tightens arms 302 against rotating element 300. Two springs 173 insure that rotating lever 170 continuously pushes against the back of patient's 4 fingers 171. It is appreciated that for larger hands 17 lever 170 is pushed away from arms 300, so to increase space to deformable element 166. In one embodiment, one spring is used to cause rotating lever 170 to continuously push against the back of the patient 4 fingers 171. In one embodiment, the spring or springs 173 have a spring constant. The value of the spring constant causes the rotating lever 170 to remain pressed against fingers 171 of the patient 4 and allow extension of the fingers 171 of the patient 4.

FIG. 18 shows a block diagram of electronic and sensing elements incorporated in therapeutic game controller 160 and including its forearm support 164. Electronics block 168 is connected to 3D tracker 161 in order to use 3D tracker 161 wireless transmitter 169 when communicating with computer 191.

Electronics block 168 receives input from finger extension rotary sensor 211, as well as pressure sensor 167 that measures air pressure inside the deformable element 166. In one embodiment, electronics 168 also receives input from a skin temperature sensor 176 that is used to measure blood flow to patient's hand 17. In one embodiment, input is received by electronics block 168 from pulse sensor 177 which measures pulse in patient's 4 forearm 26.

Electronics block 168, housed inside arm support 164 is powered by rechargeable batteries 175. In this way there are no power cables, or tethers connected to therapeutic game controller assembly 160. Such cables or tethers would otherwise impede movement of patient 4 forearm 26.

Figure 19A:
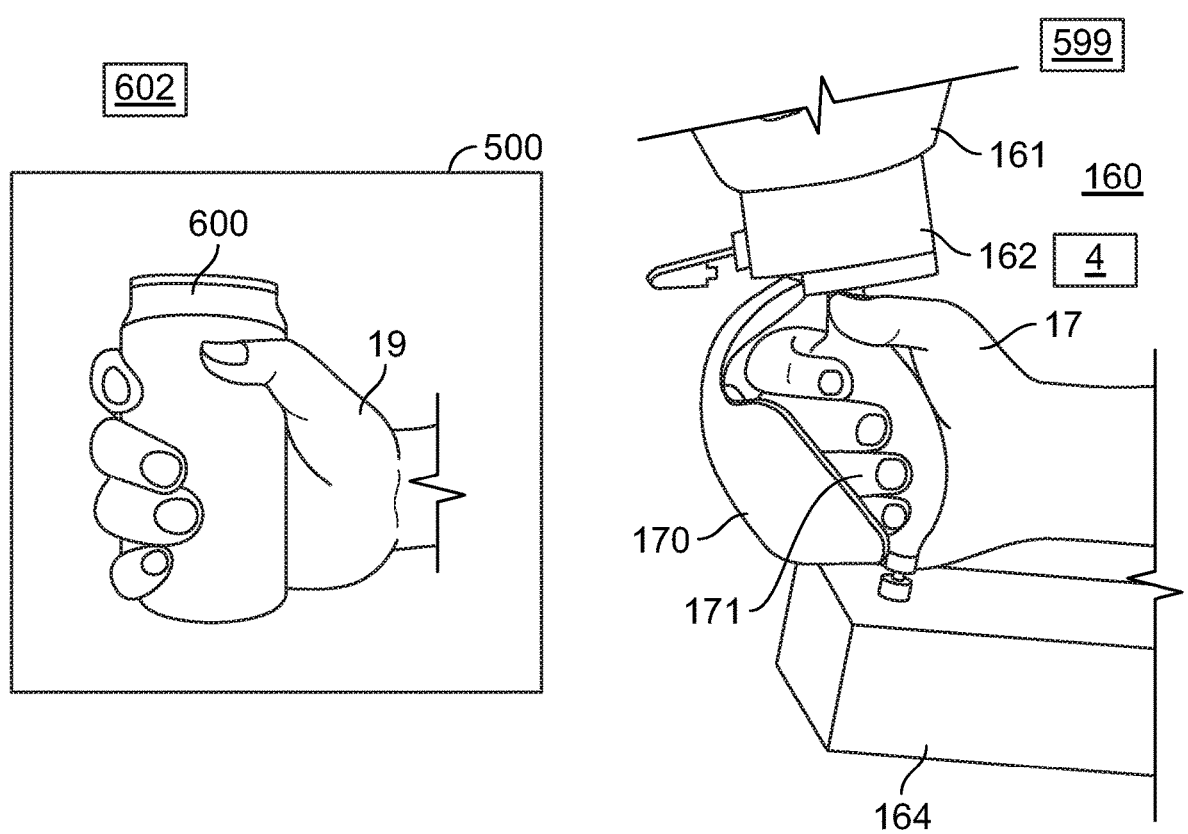
FIG. 19a illustrates a method of conveying the illusion of an object seen on the computer game screen of being a hard object, when patient power grasps a deformable element of the therapeutic game controller.

In one embodiment, patient 4 receives haptic sensorial illusion 599. Sensorial illusion 599 is obtained by varying virtual compliance 602, 603 of virtual objects grasped by hand avatar 19. As illustrated in FIG. 19a, virtual soda can 600 is shown by display 500. Hand avatar 19 is tightly wrapped around virtual soda can 600, while patient 4 grasps deformable element 166 of therapeutic game controller 160. While patient 4 fingers 171 are fully wrapped around deformable element 166 and grasping hard, virtual hand avatar 19 cannot deform virtual can 600. This gives patient 4 the illusion that hand avatar 19 squeezes can 600 that is hard.

Figure 19B:
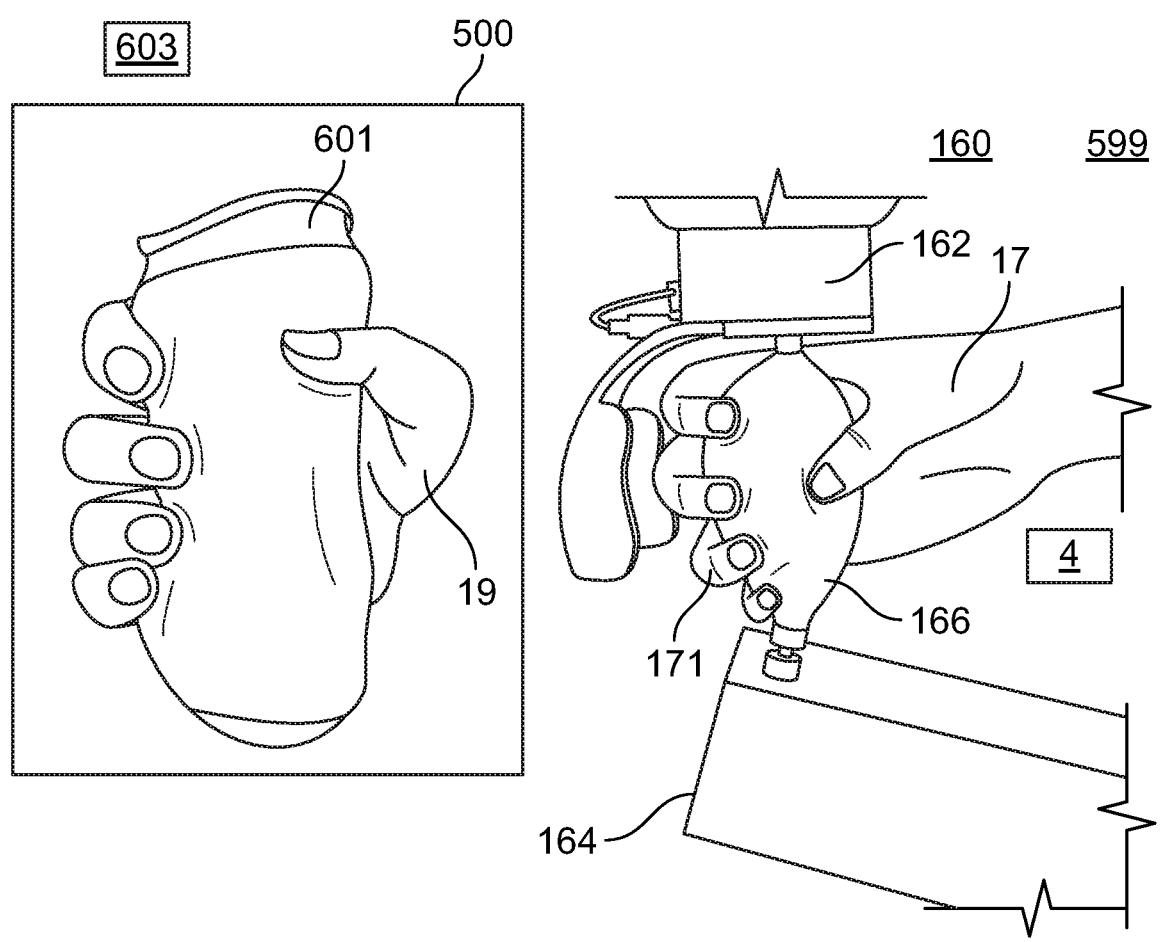
FIG. 19b illustrates a method of conveying the illusion of an object seen on the computer game screen of being a soft object, when patient holds a deformable element of the therapeutic game controller with the fingertips (precision grasps)

FIG. 19b depicts display 500 presenting hand avatar 19 grasping virtual object 601. Such object may be a soda can. On display 500 object 601 appears to be crushed by hand avatar 19. This time, in order to deform object 601 patient 4 fingers 171 barely touched deformable element 166 of therapeutic game controller 160, in what is called precision grasping. The mismatch between little force applied by patient 4 on deformable element 166 and the crushing of virtual soda can 601 by hand avatar 19, conveys the illusion that can 601 is very soft.

In one embodiment, sensorial illusion of hardness or softness of virtual objects 600, 601 may be used to distinguish two virtual objects that have identical appearance, based on their perceived hardness. Thus the sorting task in Catch 3D game 310 may be enhanced to incorporate perceived hardness of graphically identical objects 311. Patient 4 may have diminished tactile perception, thus this training modality may be used clinically to address this deficit. In one embodiment, patient 4 will be asked to sort graphically identical objects into "soft" and "hard" bins 312. Computer 191 will know the correct sorting, and percentage of erroneous placements out of total number of objects in Catch 3D game 310 will be indicative of patient 4 tactile perception deficits.

The following is a list of references referred to herein, each of which is incorporated by reference:

Reference No. 1—Roger V L, Go A S, Lloyd-Jones D M, Benjamin E J, Berry J D, Borden W B, et al. Heart disease and stroke statistics—2012 update: a report from the American Heart Association. *Circulation.* 2012; 125(1): e2-220.

Reference No. 2—C. Y. Wu, L. L. Chuang, K. C. Lin, H. C. Chen and P. K. Tsay, Randomized trial of distributed constraint-induced therapy versus bilateral arm training for the rehabilitation of upper-limb motor control and function after stroke. *Neurorehab Neural Re*, Vol. 25, 2, pp. 130-139, 2011.

Reference No. 3—J. H. Cauraugh, N. Lodha, S. K. Naik and J. J. Summers, Bilateral movement training and stroke motor recovery progress: a structured review and meta-analysis. *Hum Movement Sci, Vol* 29, 5, pp. 853-870, 2010.

Reference No. 4—C. Ausenda and M. Carnovali, Transfer of motor skill learning from the healthy hand to the paretic hand in stroke patients: a randomized controlled trial. *Eur J Phys Rehabil Med*, Vol. 47, 3, pp. 417-425, 2011.

Reference No. 5—G. Burdea, Virtual rehabilitation-benefits and challenges. *J Meth Inform Med*, pp. 519-523, 2003.

Reference No. 6—C. Brooks, B. Gabella, R. Hoffman, D. Sosin, and G. Whiteneck, Traumatic brain injury: designing and implementing a population-based follow-up system. *Arch Phys Med Rehab*, 78, pp. S26-S30, 1997.

Reference No. 7—M. Wang, N. J. Gamo, Y. Yang, L. E. Jin, X. J. Wang, et al., Neuronal basis of age-related working memory decline, *Nature*, Vol 476, pp. 210-213, July, 2011.

Reference No. 8—G. Burdea, K. Polistico, R. Liu, G. House, R. Muniz, N. Macaro, L. Slater, J. Hundal, "BrightBrainer feasibility study in a medical adult day program," Int. Conf. Virtual Rehabilitation, Valencia, Spain. June 2015, 57-64.

Reference No. 9—к. Lin, Y. Chen, C. Chen, C. Y. Wu and Y. F. Chang, The effects of bilateral arm training on motor control and functional performance in chronic stroke: a randomized controlled study, *Neurorehab Neural Re*, Vol 24; pp. 42-51, 2010.

Reference No. 10—P. W. Duncan, M. Probst, and S. G. Nelson, Reliability of the Fugl-Meyer assessment of sensorimotor recovery following cerebrovascular accident. *Phys Ther*, Vol 63, pp. 1606-1610, 1983.

Reference No. 11—G. Optale, C. Urgesi, V. Busato, S. Marin, L. Piron et al., Controlling memory impairment in elderly adults using virtual reality memory training: a randomized controlled pilot study. *Neurorehab Neural Re*, Vol 24, 4, pp. 348-357, 2010.

Reference No. 12—Unity Technologies, Reference Manual. San Francisco, Calif., 2010.

Reference No. 13—Sixense Entertainment, Razer Hydra Master Guide, 11 pp., 2011.

Reference No. 14—CNet Leap Motion controller review: Virtual reality for your hands. Jul. 22, 2013. http://reviews.cnet.com/input-devices/leap-motion-controller/4505-3133_7-35823002.html.

Reference No. 15—G. Burdea and M. Golomb, U.S. patent application Ser. No. 12/422,254 "Method for treating and exercising patients having limited range of body motion, Apr. 11, 2009.

Reference No. 16—G. Burdea, D. Cioi, J. Martin, D. Fensterheim and M. Holenski, The Rutgers Arm II rehabilitation system—a feasibility study, *IEEE Trans Neural Sys Rehab Eng*, Vol 18, 5, pp. 505-514, 2010.

Reference No. 17—G. Burdea, C. Defais, K. Wong, J. Bartos and J. Hundal, "Feasibility study of a new game-based bimanual integrative therapy," Proceedings 10$^{th}$ Int. Conference on Virtual Rehabilitation, Philadelphia, Pa., August 2013, pp. 101-108.

Reference No. 18—G. Burdea, K. Polistico, A. Krishnamoorthy, J. Hundal, F. Damiani, S. Pollack, "A Feasibility study of BrightBrainer™ cognitive therapy for elderly nursing home residents with dementia," Disability and Rehabilitation—Assistive Technology. 10(5):421-32, 2015.

Reference No. 19—Raghavan P, "Upper Limb Motor Impairment After Stroke," Physical Medicine and Rehabilitation Clinics of North America, 26(4):599-610, 2015.

While various embodiments have been described with respect to specific examples, those skilled in the art will appreciate that there are numerous variations and permutations of the above described systems and techniques. It is to be understood that other embodiments may be utilized and structural and functional modifications may be made without departing from the scope of the present disclosure. Thus, the spirit and scope of the subject matter of the disclosure should be construed broadly as set forth in the appended claims and in view of the specification.

The invention claimed is:

1. A method of providing therapy to a user having an arm and a hand comprising:
   providing a hand-held controller comprising a 3D movement sensor configured to detect movement of the hand-held controller, a grip sensor attached to the movement sensor and engageable by the user, and a finger extension sensor attached to the movement sensor and engageable by the user, at least a portion of the finger extension sensor being forced toward the grip sensor and one or more fingers of the user when the user grips the grip sensor, wherein the finger extension sensor comprises a rotating mechanical lever;
   executing a video game on a computer and portraying action from the video game on a display, the action being viewable by the user, the user holding the hand-held controller;
   sending, from the hand-held controller, one or more signals representative of data from one or more of the movement sensor, the grip sensor, and the finger extension sensor to the computer, and analyzing, at the computer, the one or more signals; and
   controlling, by the computer, action portrayed on the display based on the one or more signals.

2. The method of claim 1, wherein the hand-held controller further comprises a forearm support, a skin temperature sensor, and a pulse sensor, the one or more signals representative of data further comprising data from at least one of the skin temperature sensor and the pulse sensor.

3. A hand-held controller comprising:
   a movement sensor configured to detect movement of the hand-held controller;
   a grip sensor attached to the movement sensor and engageable by a user; and
   a finger extension sensor attached to the movement sensor and engageable by a user, at least a portion of the finger extension sensor being forced toward the grip sensor and one or more fingers of the user when the user grips the grip sensor,
   wherein the finger extension sensor comprises a rotating mechanical lever.

4. The hand-held controller of claim 3, further comprising:
   a forearm support attached to the movement sensor;
   a skin temperature sensor attached to the forearm support; and
   a pulse sensor attached to the forearm support.

5. The hand-held controller of claim 3, wherein the movement sensor comprises a 3D tracker configured to measure a position and an orientation of the movement sensor.

6. The hand-held controller of claim 5, wherein the position and orientation of the movement sensor is associated with one of an arm and a hand of a user.

7. The hand-held controller of claim 3, wherein the grip sensor comprises a sealed air chamber.

8. The hand-held controller of claim 7, wherein the sealed air chamber has a bulb shape.

9. The hand-held controller of claim 3, wherein the rotating mechanical lever comprises a rotary sensor configured to sense movement of the rotating mechanical lever.

10. The hand-held controller of claim 9, wherein the finger extension sensor comprises a spring having a spring constant, the spring constant having a value causing the rotating mechanical lever to remain pressed against fingers of a user and allow extension of the fingers of the user.

11. A system comprising:
a hand-held controller comprising:
   a movement sensor configured to detect movement of the hand-held controller;
   a grip sensor attached to the movement sensor and engageable by a user; and
   a finger extension sensor connected to the movement sensor and engageable by a user, at least a portion of the finger extension sensor being forced toward the grip sensor and one or more fingers of the user when the user grips the grip sensor;
a computer in communication with the hand-held controller;
and a display in communication with the computer,
wherein the finger extension sensor comprises a rotating mechanical lever.

12. The system of claim 11, further comprising:
a forearm support attached to the movement sensor;
a skin temperature sensor attached to the forearm support; and
a pulse sensor attached to the forearm support.

13. The system of claim 12, wherein the computer receives one or more signals from the hand-held controller and transmits signals to the display, the signals transmitted to the display comprising a graphical representation based on the one or more signals received from the hand-held controller.

14. The system of claim 12, wherein the movement sensor comprises a 3D tracker configured to measure a position and an orientation of the movement sensor.

15. The system of claim 14, wherein the position and orientation of the movement sensor is associated with one of an arm and a hand of a user.

16. The system of claim 12, wherein the forearm support is attached to the movement sensor by an attachment member passing through the grip sensor.

17. The system of claim 12, further comprising:
a second hand-held controller in communication with the computer, wherein the second hand-held controller sends one or more signals representative of controller data to the computer and the computer analyzes the controller data and controls action portrayed on the display based on the controller data.

18. The system of claim 11, wherein the grip sensor comprises a sealed air chamber.

19. The system of claim 18, wherein the sealed air chamber has a bulb shape.

20. The system of claim 11, wherein the rotating mechanical lever comprises a rotary sensor configured to sense movement of the rotating mechanical lever.

21. The system of claim 20, wherein the finger extension sensor comprises a spring having a spring constant, the spring constant having a value causing the rotating mechanical lever to remain pressed against fingers of a user and allow extension of the fingers of the user.

22. The system of claim 11, wherein the finger extension sensor comprises an adjustment mechanism that is used to adjust for a hand size of a user.

23. The system of claim 22, wherein the adjustment mechanism comprises a mechanical wheel tightening matching arms of the finger extension sensor to those of a rotating sensor support.

* * * * *